(12) United States Patent
Giwercman

(10) Patent No.: US 8,604,059 B2
(45) Date of Patent: Dec. 10, 2013

(54) THIOXANTHENE DERIVATIVES FOR THE TREATMENT OF INFECTIOUS DISEASES

(75) Inventor: Birgit Kjældgaard Giwercman, Charlottenlund (DK)

(73) Assignee: BKG Pharma APS, Charlottenlund (DK)

( * ) Notice: Subject to any disclaimer, the term of this patent is extended or adjusted under 35 U.S.C. 154(b) by 0 days.

(21) Appl. No.: 13/265,149

(22) PCT Filed: Apr. 20, 2010

(86) PCT No.: PCT/EP2010/055176
§ 371 (c)(1),
(2), (4) Date: Feb. 2, 2012

(87) PCT Pub. No.: WO2010/122012
PCT Pub. Date: Oct. 28, 2010

(65) Prior Publication Data
US 2012/0122880 A1     May 17, 2012

Related U.S. Application Data

(60) Provisional application No. 61/202,918, filed on Apr. 20, 2009.

(30) Foreign Application Priority Data

Apr. 20, 2009 (EP) .................................... 09158229

(51) Int. Cl.
*A61K 31/445* (2006.01)
*C07D 409/06* (2006.01)

(52) U.S. Cl.
USPC ........... 514/324; 546/184; 546/195; 546/202; 514/315; 514/317; 514/320

(58) Field of Classification Search
USPC ........... 546/184, 195, 202; 514/315, 320, 324
See application file for complete search history.

(56) References Cited

U.S. PATENT DOCUMENTS

| | | | |
|---|---|---|---|
| 3,055,888 A | 9/1962 | Renz et al. | |
| 3,449,334 A | 6/1969 | Zirkle | |
| 7,544,681 B2 * | 6/2009 | Nudelman et al. | ......... 514/225.2 |
| 2004/0265903 A1 | 12/2004 | Mueller et al. | |

FOREIGN PATENT DOCUMENTS

| | | |
|---|---|---|
| DE | 10 2006 030 835 B3 | 10/2007 |
| EP | 0 338 532 A2 | 10/1989 |
| EP | 0 479 488 A2 | 4/1992 |
| WO | 2005105145 A1 | 11/2005 |
| WO | 2008/080408 A1 | 7/2008 |

OTHER PUBLICATIONS

Giwercman et al (2008): STN International HCAPLUS database, Columbus (OH), accession No. 2008:824779.*
Krasney et al (1992): STN International HCAPLUS database, Columbus (OH), accession No. 1993:32933.*
Kaatz, G. W., et al., "Phenothiazines and Thioxanthenes Inhibit Multidrug Efflux Pump Activity in *Staphylococcus aureus*", Antimicrobial Agents and Chemotherapy, vol. 47, No. 2, p. 719-726, (2003).
Muren, J. F., et al., "Thioxanthene Psychopharmacological Agents. II. 9-(3-Aminopropylidene)-N,N-dimethylthioxanthene-2-sulfonamides", Journal of Medicinal Chemistry, vol. 13, No. 1, p. 17-23, (1970).
Ragland, J. B., et al., "Spectrofluorometric Measurement of Phenothiazines", Anal. Chem., vol. 36, No. 7, p. 1356-1359, (1964).
Kristiansen, J. E., et al., "Inhibition of HIV replication by neuroleptic agents and their potential use in HIV infected patients with AIDS related dementia", International Journal of Antimicrobial Agents, vol. 14, p. 209-213, (2000).
Kolaczkowski, M., et al., "Phenothiazines as potent modulators of yeast multidrug resistance", International Journal of Antimicrobial Agents, vol. 22, p. 279-283, (2003).

* cited by examiner

*Primary Examiner* — Golam M M Shameem
(74) *Attorney, Agent, or Firm* — Nath, Goldberg & Meyer; Tanya E. Harkins

(57) ABSTRACT

The claimed subject matter is directed to certain thioxanthene derivatives and phenothiazine derivatives suitable for use as anti-infective agents, in particular, for the treatment of infectious diseases. The claimed subject matter furthermore relates to compositions including said anti-infective agents.

11 Claims, No Drawings

THIOXANTHENE DERIVATIVES FOR THE TREATMENT OF INFECTIOUS DISEASES

This is a National Phase Application filed under 35 U.S.C. §371 as a national stage of PCT/EP2010/055176, filed on Apr. 20, 2010, an application claiming the benefit under 35 U.S.C. §119 of European Patent Application No. 09158229.6, filed on Apr. 20, 2009, and an application claiming the benefit under 35 U.S.C. §119(e) of U.S. Provisional Application No. 61/202,918, filed on Apr. 20, 2009, the content of each of which is hereby incorporated by reference in its entirety.

TECHNICAL FIELD

The present invention is directed to anti-infective agents, in particular thioxanthene and phenothiazine derivatives, as well as the use thereof for treatment of infectious diseases. Furthermore, the invention relates to the use of the compounds according to the invention as chemosensitising compounds.

BACKGROUND

The treatment of infectious diseases is a major clinical concern worldwide. As infectious agents become resistant to more and more antibiotic compounds, the development of new and more efficient infectious agents is a major task in the art. Resistance to chemotherapy is a common clinical problem in patients with infectious diseases. During the treatment of infections, the drug targets of prokaryotic or eukaryotic microorganism cells are often found to be refractory to a variety of drugs that have different structures and functions. This phenomenon has been referred to as multidrug resistance (MDR).

The incidence of the multiple antimicrobial resistance of bacteria which cause infections in hospitals/intensive care units is increasing, and finding microorganisms insensitive to more than 10 different antibiotics is not unusual. Examples of such resistant bacteria include methicillin-resistant and methicillin-vancomycin-resistant *Staphylococcus aureus*; vancomycin-resistant enterococci, such as *Enterococcus faecalis* and *Enterococcus faecium*; penicillin-resistant *Streptococcus pneumoniae*, and cephalosporin and quinolone resistant gram-negative rods (coliforms), such as *E. coli, Salmonella* species, *Klebsiella pneumoniae, Pseudomonas* species and *Enterobacter* species. More recently, pan antibiotic resistant gram-negative and gram-positive bacilli have emerged.

The rapidity of emergence of these multiple antibiotic-resistant bacteria is not being reflected by the same rate of development of new antibiotics, and it is therefore conceivable that patients with serious infections soon will no longer be treatable with the currently available anti-infective agents. Several international reports have highlighted the potential problems associated with the emergence of antimicrobial resistance in many areas of medicine and also outlined the difficulties in the management of patients with infections caused by these microorganisms.

Although most of the hardier microorganisms are present in hospitals, strains of multidrug resistant bacteria, such as *Streptococcus pneumoniae* and *Mycobacterium tuberculosis* have also caused serious community-acquired infections. The prevalence of drug-resistant *Streptococcus pneumoniae* has increased 60-fold since 1980 with 51% and 8% of isolates demonstrating intermediate- or high-level resistance to penicillin or third-generation cephalosporins, respectively. Thus, pneumococcal pneumonia is becoming more difficult to treat with first-line anti-infective agents. Resistant bacteria from hospitals can be introduced into the community via patients discharged for continued treatment at home taking with them, for example, multidrug resistant *Staphylococcus aureus* and vancomycin resistant enterococci.

Phenothiazines and thioxanthenes are used clinically as neuroleptic and antiemetic agents. Phenothiazines, and structurally related antipsychotic agents, inhibit several cellular enzymes and block the function of critical cellular receptors. The extrapyramidal side effects associated with antipsychotic therapy are attributed to dopamine receptor binding. In general, these extrapyramidal side effects have proven to be dose limiting in clinical trials using phenothiazines and thioxanthenes in non-psychotic areas, such as anti-cancer treatment. The relevant serum levels of phenothiazines and thioxanthenes are generally in the range from approximately 0.3 µg/l to 0.5 mg/l (0.3 ng/ml to 0.5 µg/ml) in order to avoid potential side effects.

Phenothiazines and thioxanthenes have been shown in themselves to have modest, but broad, antimicrobial activities. MICs (the minimal concentration of compound at which the infectious agent is inhibited) are generally high above clinically relevant concentrations inasmuch as the disclosed minimum effective concentrations in vitro are in the order from approximately 20 mg/l to several hundreds mg/l. Although the mechanism by which phenothiazines modulate MDR is not yet clear, it has been suggested that their pharmacological properties may be mediated at least in part by the inhibition of efflux pumps. Also, promethazine has been recognised as an effective antiplasmid agent in cultures containing bacterial species such as *Escherichia coli, Yersinia enterocolitica, Staphylococcus aureus* and *Agrobacterium tumefaciens*. The concentrations used, however, are generally high above clinically relevant concentrations.

It has recently been shown that certain phenothiazine and thioxanthene derivatives used as anti-infective compounds are surprisingly effective in assisting in killing infectious agents, such as multidrug resistant infectious agents, even at clinically relevant concentrations, when used in combination with an anti-infective agent.

Accordingly, WO2005/105145 A discloses the use of certain thioxanthene derivatives and phenothiazine derivatives as chemosensitising compounds. Chemosensitising compounds are anti-infectious compounds for the treatment of infectious disease in combination with an anti-infectious agent. The disclosed derivatives all have a nitrogen containing substituent on the thioxanthene or phenothiazine backbone. The problem solved according to that disclosure relates to a combination treatment of infective diseases and does not teach that the disclosed compounds are suited for administration as single anti-bacterial agents but rather that the disclosed compounds are suited for a combination treatment where another antibiotic agent is used simultaneously in combination with the disclosed compounds. The compounds according to the present invention differ from the compounds according to WO2005/105145 A e.g. in the substitution of C for N in the atom linking substituents $R_9$ and $R_{10}$ according to the present invention.

WO2008/080408 A discloses the surprising finding that a sub-group of the compounds disclosed in WO2005/105145 A may in fact be useful as sole antibacterial agents. This finding is surprising as it was thought that the function of the compounds according to WO2005/105145 A as chemosensitising compounds was to reverse resistance against one or more anti-infectious agent.

EP-A-0338532 discloses the use of clopenthixol among other compounds as an anti-protozoal agent.

Kolaczkowski M et al., International Journal of Antimicrobial Agents (2003) Vol. 2, No. 3 discloses trans-flupenthixol among a range of compounds as modulators of yeast multidrug resistance.

Kristensen et al., International Journal of Antimicrobial Agents (2000) Vol. 14, No. 3 discloses cis- and trans-flupenthixol as HIV-inhibitors.

It is clear that the increase in resistance to anti-infective agents, such as antibiotics, present a major impediment to the treatment of infections. Thus, there is an urgent need for new anti-infective agents. There is also a need for compounds inhibiting and reversing drug resistance and development of drug resistance in infective agents.

The object of the present invention is to provide anti-infective agents capable of killing or inhibiting growth of clinically relevant microorganisms, especially resistant, including multidrug resistant, cells or microorganisms by the administration of clinically relevant amounts of such anti-infective agents to a subject in need thereof.

Further, an object of the present invention was to provide chemosentisising agents capable of, in combination with an additional anti-infective agent, killing or inhibiting growth of clinically relevant microorganisms, especially resistant, including multidrug resistant, cells or microorganisms by the administration of clinically relevant amounts of such anti-infective agents to a subject in need thereof.

DISCLOSURE OF THE INVENTION

It has surprisingly been found that certain novel thioxanthene and phenotiazine compounds, alternative to the compounds disclosed in WO2005/105145 A, are also suitable and even superior for use in the treatment of infectious diseases.

Surprisingly, it was found that by applying clinically relevant amounts of the novel anti-infective agents described herein, effective killing of microorganisms, including resistant or multidrug resistant clinically relevant isolates was achieved. Contrary to what was previously believed, this surprising finding opens up the possibility for effectively combating microorganisms by use of the anti-infective agents described herein as sole anti-infective agent. Further, it was shown that the compounds according to the invention are useful as chemosensitising compounds.

Accordingly, in a first aspect, the present invention relates to a compound of the general formula (I)

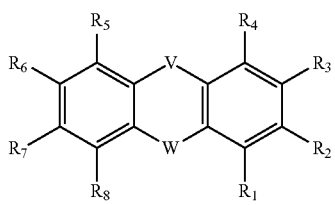

wherein
V is selected from the group consisting of S, $SO_2$, SO, O and NH;
W is N—$(CHX)_m$—$CX(R_9)(R_{10})$ or W is N—$(CHX)_{m-1}$—CH=$C(R_9)(R_{10})$ or W is C=CH—$(CHX)_n$—$CX(R_9)(R_{10})$ or W is C=CH—$(CHX)_{n-1}$—CH=$C(R_9)(R_{10})$;
m is an integer in the range of from 1 to 6;
n is an integer in the range of from 1 to 5;
each X is individually selected from the group consisting of hydrogen, halogen, hydroxy, amino, nitro, optionally substituted $C_{1-6}$-alkyl and optionally substituted $C_{1-6}$-alkoxy;
$R_1$, $R_2$, $R_3$, $R_4$, $R_5$, $R_6$, $R_7$ and $R_8$ are each individually selected from the group consisting of hydrogen, halogen, hydroxy, amino, nitro, optionally substituted $C_{1-6}$-alkyl, optionally substituted $C_{2-6}$-alkenyl, optionally substituted $C_{2-6}$-alkynyl and optionally substituted $C_{1-6}$-alkoxy, optionally substituted $C_{2-6}$-alkenyloxy, carboxy, optionally substituted $C_{1-6}$-alkoxycarbonyl, optionally substituted $C_{1-6}$-alkylcarbonyl, formyl, optionally substituted $C_{1-6}$-alkylsulphonylamino, optionally substituted aryl, optionally substituted aryloxycarbonyl, optionally substituted aryloxy, optionally substituted arylcarbonyl, optionally substituted arylamino, arylsulphonylamino, optionally substituted heteroaryl, optionally substituted heteroaryloxycarbonyl, optionally substituted heteroaryloxy, optionally substituted heteroarylcarbonyl, optionally substituted heteroarylamino, heteroarylsulphonylamino, optionally substituted heterocyclyl, optionally substituted heterocyclyloxycarbonyl, optionally substituted heterocyclyloxy, optionally substituted heterocyclylcarbonyl, optionally substituted heterocyclylamino, heterocyclylsulphonylamino, mono- and di($C_{1-6}$-alkyl) amino, carbamoyl, mono- and di($C_{1-6}$-alkyl)aminocarbonyl, amino-$C_{1-6}$-alkyl-aminocarbonyl, mono- and di($C_{1-6}$-alkyl) amino-$C_{1-6}$-alkyl-aminocarbonyl, $C_{1-6}$-alkylcarbonylamino, amino-$C_{1-6}$-alkyl-carbonylamino, mono- and di($C_{1-6}$-alkyl) amino-$C_{1-6}$-alkyl-carbonylamino, amino-$C_{1-6}$-alkyl-amino, mono- and di($C_{1-6}$-alkyl)amino-$C_{1-6}$-alkyl-amino, cyano, guanidino, carbamido, $C_{1-6}$-alkanoyloxy, $C_{1-6}$-alkylsulphonyl, $C_{1-6}$-alkylsulphinyl, $C_{1-6}$-alkylsulphonyloxy, aminosulfonyl, mono- and di($C_{1-6}$-alkyl)aminosulfonyl, and optionally substituted $C_{1-6}$-alkylthio; and $R_9$ and $R_{10}$ are each independently selected from the group consisting of hydrogen, optionally substituted $C_{1-6}$-alkyl, optionally substituted $C_{2-6}$-alkenyl, optionally substituted $C_{2-6}$-alkynyl, optionally substituted $C_{1-6}$-alkoxycarbonyl, optionally substituted $C_{1-6}$-alkylcarbonyl, optionally substituted aryl, optionally substituted aryloxycarbonyl, optionally substituted arylcarbonyl, optionally substituted heteroaryl, optionally substituted heteroaryloxycarbonyl, optionally substituted heteroarylcarbonyl, aminocarbonyl, mono- and di($C_{1-6}$-alkyl)aminocarbonyl;

or $R_9$ and $R_{10}$ together with the carbon atom to which they are attached form an optionally substituted aryl group, or an optionally substituted $C_{3-6}$-cycloalkyl or an optionally substituted $C_{3-6}$-heterocyclyl, preferably a nitrogen-containing heteroaryl or a nitrogen-containing optionally substituted heterocyclyl;

or a metabolite or salt thereof.

In a preferred aspect of the invention, W is C=CH—$(CHX)_n$—$CX(R_{10})(R_{10})$ or C=CH—$(CHX)_{n-1}$—CH=C $(R_9)(R_{10})$ In a preferred aspect the present invention relates to an anti-infective agent of the general formula (II)

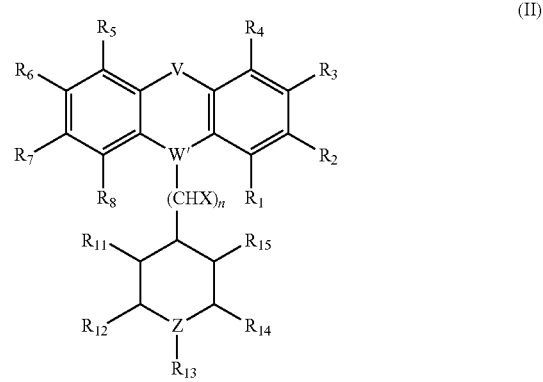

wherein

V is selected from the group consisting of S, $SO_2$, SO, O and NH;

W' is N or C=CH;

n is an integer in the range of from 1 to 6;

each X is individually selected from the group consisting of hydrogen, halogen, hydroxy, amino, nitro, optionally substituted $C_{1-6}$-alkyl and optionally substituted $C_{1-6}$-alkoxy;

Z is selected among C, N, S or O;

$R_1$, $R_2$, $R_3$, $R_4$, $R_5$, $R_6$, $R_7$, $R_8$, $R_{11}$, $R_{12}$, $R_{14}$ and $R_{15}$ are each individually selected from the group consisting of hydrogen, halogen, hydroxy, amino, nitro, optionally substituted $C_{1-6}$-alkyl, optionally substituted $C_{2-6}$-alkenyl, optionally substituted $C_{2-6}$-alkynyl and optionally substituted $C_{1-6}$-alkoxy, optionally substituted $C_{2-6}$-alkenyloxy, carboxy, optionally substituted $C_{1-6}$-alkoxycarbonyl, optionally substituted $C_{1-6}$-alkylcarbonyl, fomyl, optionally substituted $C_{1-6}$-alkylsulphonylamino, optionally substituted aryl, optionally substituted aryloxycarbonyl, optionally substituted aryloxy, optionally substituted arylcarbonyl, optionally substituted arylamino, arylsulphonylamino, optionally substituted heteroaryl, optionally substituted heteroaryloxycarbonyl, optionally substituted heteroaryloxy, optionally substituted heteroarylcarbonyl, optionally substituted heteroarylamino, heteroarylsulphonylamino, optionally substituted heterocyclyl, optionally substituted heterocyclyloxycarbonyl, optionally substituted heterocyclyloxy, optionally substituted heterocyclylcarbonyl, optionally substituted heterocyclylamino, heterocyclylsulphonylamino, mono- and di($C_{1-6}$-alkyl)amino, carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, amino-$C_{1-6}$-alkyl-carbonylamino, mono- and di($C_{1-6}$-alkyl)amino-$C_{1-6}$-alkyl-carbonylamino, amino-$C_{1-6}$-alkyl-amino, mono- and di($C_{1-6}$-alkyl)amino-$C_{1-6}$-alkyl-amino, cyano, guanidino, carbamido, $C_{1-6}$-alkanoyloxy, $C_{1-6}$-alkylsulphonyl, $C_{1-6}$-alkylsulphinyl, $C_{1-6}$-alkylsulphonyloxy, aminosulfonyl, mono- and di($C_{1-6}$-alkyl)aminosulfonyl, and optionally substituted $C_{1-6}$-alkylthio; and $R_{13}$ is hydrogen, halogen, hydroxy, amino, nitro, optionally substituted $C_{1-6}$-alkyl or optionally substituted $C_{1-6}$-alkoxy;

or a salt thereof.

As will be immediately obvious to the skilled person, the carbon atoms in the $(CHX)_n$ chain linking the phenothiazine or thioxanthene backbone with the group consisting of $R_9$ and $R_{10}$, or the 6-membered heterocyclyl shown above in formula II, together with the carbon atom to which they are attached, may be linked by double bonds instead of single bonds (at the expense of 2×H) if appropriate without thereby departing from the inventive scope of the present invention.

The compounds according to the invention are anti-infective agents. They are useful for the treatment or prophylaxis of an infectious disease. They may further be used for the manufacture of a medicament for the treatment or prophylaxis of an infectious disease. The may be used as a sole active ingredient. They may also be used as an anti-infective active ingredient in combination with another anti-infective agent. They may also be used as chemosensitising compounds in combination with another anti-infective agent.

In a preferred aspect, W' is C=CH and $R_{12}$ is hydrogen, hydroxy, amino, nitro, halogen, $CH_2Y$, $CHY_2$ and $CY_3$, wherein Y is a halogen atom;

In one preferred aspect, the present invention relates to an anti-infective agent of the formula

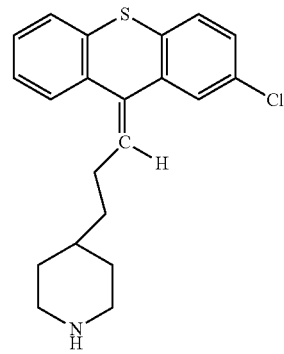

In another preferred aspect, the present invention relates to an anti-infective agent of the formula

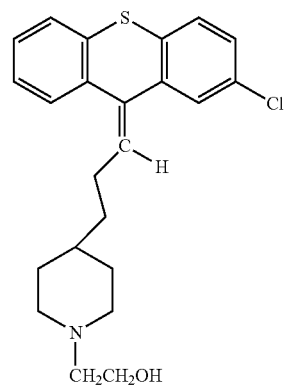

Other aspect of the present invention will be apparent from the description below and the appended claims.

DETAILED DESCRIPTION OF THE INVENTION

Definitions

In the present context, the term "$C_{1-6}$-alkyl" is intended to mean a linear or branched saturated hydrocarbon group having from one to six carbon atoms, such as methyl, ethyl, n-propyl, isopropyl, n-butyl, isobutyl, sec-butyl, tert-butyl, n-pentyl, isopentyl, neopentyl and n-hexyl.

In the present context, the term "$C_{3-6}$-cycloalkyl" is intended to cover three-, four-, five- and six-membered rings comprising carbon atoms only, whereas the term "heterocyclyl" is intended to mean three-, four-, five- and six-membered rings wherein carbon atoms together with from 1 to 3 heteroatoms constitute said ring. The heteroatoms are independently selected from oxygen, sulphur, and nitrogen. $C_{3-6}$-cycloalkyl and heterocyclyl rings may optionally contain one or more unsaturated bonds situated in such a way, however, that an aromatic π-electron system does not arise.

Illustrative examples of "$C_{3-6}$-cycloalkyl" are the carbocycles cyclopropane, cyclobutane, cyclopentane, cyclopentene, cyclopentadiene, cyclohexane, cyclohexene, 1,3-cyclohexadiene and 1,4-cyclohexadiene.

Illustrative examples of "heterocyclyls" are the nitrogen-containing heterocycles 2-pyrrolinyl, 3-pyrrolinyl, pyrrolidinyl, 2-imidazolinyl, imidazolidinyl, 2-pyrazolinyl, 3-pyrazolinyl, pyrazolidinyl, piperidinyl, morpholinyl, thiomorpholinyl and piperazinyl. Binding to the heterocycle may be at the position of the heteroatom or via a carbon atom of the heterocycle.

In the present context, the term "$C_{2-6}$-alkenyl" is intended to mean a linear or branched hydrocarbon group having from two to six carbon atoms and containing one or more double bonds. Illustrative examples of $C_{2-6}$-alkenyl groups include allyl, homo-allyl, vinyl, crotyl, butenyl, pentenyl and hexenyl. Illustrative examples of $C_{2-6}$-alkenyl groups with more than one double bond include butadienyl, pentadienyl and hexadienyl. The position of the double bond(s) may be at any position along the carbon chain.

In the present context, the term "$C_{2-6}$-alkynyl" is intended to mean a linear or branched hydrocarbon group containing from two to six carbon atoms and containing one or more triple bonds. Illustrative examples of $C_{2-6}$-alkynyl groups include acetylene, propynyl, butynyl, pentynyl and hexynyl. The position of the triple bond(s) may be at any position along the carbon chain. More than one bond may be unsaturated so that the "$C_{2-6}$-alkynyl" is a di-yne or enedi-yne as is known to the person skilled in the art.

When used herein the term "$C_{1-6}$-alkoxy" is intended to mean $C_{1-6}$-alkyl-oxy, such as methoxy, ethoxy, n-propoxy, isopropoxy, n-butoxy, isobutoxy, sec-butoxy, tert-butoxy, n-pentoxy, isopentoxy, neopentoxy and n-hexoxy.

The term "halogen" includes fluorine, chlorine, bromine and iodine.

In the present context, the term "aryl" is intended to mean a carbocyclic aromatic ring or ring system. Moreover, the term "aryl" includes fused ring systems wherein at least two aryl rings, or at least one aryl and at least one $C_{3-6}$-cycloalkyl, or at least one aryl and at least one heterocyclyl share at least one chemical bond. Illustrative examples of "aryl" rings include phenyl, naphthalenyl, phenanthrenyl, anthracenyl, acenaphthylenyl, tetralinyl, fluorenyl, indenyl, indolyl, coumaranyl, coumarinyl, chromanyl, isochromanyl, and azulenyl.

In the present context, the term "heteroaryl" is intended to mean an aryl group where one or more carbon atoms in an aromatic ring have been replaced with one or more heteroatoms selected from the group consisting of nitrogen, sulphur, phosphorous and oxygen. Furthermore, in the present context, the term "heteroaryl" comprises fused ring systems wherein at least one aryl ring and at least one heteroaryl ring, at least two heteroaryls, at least one heteroaryl and at least one heterocyclyl, or at least one heteroaryl and at least one $C_{3-6}$-cycloalkyl share at least one chemical bond.

Illustrative examples of a heteroaryl include furanyl, thienyl, pyrrolyl, phenoxazonyl, oxazolyl, thiazolyl, isothiazolyl, imidazolyl, pyrazolyl, isoxazolyl, imidazolyl isothiazolyl, oxadiazolyl, furazanyl, triazolyl, thiadiazolyl, piperidinyl, pyridinyl, pyridazinyl, pyrimidinyl, pyrazinyl, pyrazolyl and triazinyl, isoindolyl, indolinyl, benzofuranyl, benzothiophenyl, benzopyrazolyl, indazolyl, benzimidazolyl, benzthiazolyl, purinyl, quinolizinyl, quinolinyl, isoquinolinyl, cinnolinyl, phthalazinyl, quinazolinyl, quinoxalinyl, naphthyridinyl, pteridinylthienofuranyl, carbazolyl, acridinyl, phenazinyl, phenothiazinyl, phenoxazinyl and thianthrenyl.

In the present context, the term "optionally substituted" is intended to mean that the group in question may be substituted one or several times, such as 1 to 5 times, preferably 1 to 3 times, most preferably 1 to 2 times, with one or more groups selected from the group consisting of $C_{1-6}$-alkyl, $C_{1-6}$-alkoxy, oxo (which may be represented in the tautomeric enol form), carboxyl, amino, hydroxy (which when present in an enol system may be represented in the tautomeric keto form), nitro, sulphono, sulphanyl, $C_{1-6}$-carboxyl, $C_{1-6}$-alkoxycarbonyl, $C_{1-6}$-alkylcarbonyl, formyl, aryl, aryloxy, aryloxycarbonyl, arylcarbonyl, heteroaryl, amino, mono- and di($C_{1-6}$-alkyl)amino, carbamoyl, mono- and di($C_{1-6}$-alkyl) aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, cyano, guanidino, carbamido, $C_{1-6}$-alkanoyloxy, $C_{1-6}$-alkylsulphonyloxy, dihalogen-$C_{1-6}$-alkyl, trihalogen-$C_{1-6}$-alkyl and halogen, where aryl and heteroaryl substituents may themselves be substituted 1-3 times with $C_{1-6}$-alkyl, $C_{1-6}$-alkoxy, nitro, cyano, hydroxy, amino or halogen. In general, the above substituents may be susceptible to further optional substitution.

The term "infectious agent" is intended to mean pathogenic microorganisms, such as bacteria, viruses, fungi and intra- or extra-cellular parasites. In a preferred aspect of the invention, the term "infectious agent" is intended to mean pathogenic microorganisms such as bacteria, fungi and vira. In a more preferred aspect of the invention the term, "infectious agent" is intended to mean only pathogenic bacteria, fungi and vira. In an even more preferred aspect of the invention, the term "infectious agent" is intended to mean only pathogenic bacteria, fungi and vira. In one aspect of the invention, the term "infectious agent" is intended to mean only pathogenic bacteria. In one aspect of the invention the term "infectious agent" is intended to mean only pathogenic fungi. In one aspect of the invention the term "infectious agent" is intended to mean only pathogenic vira.

Analogously, the term "infectious disease" is used about a disease caused by an infectious agent.

In the present context, the term "anti-infective agent" covers agents that are capable of killing, inhibiting or otherwise slowing the growth of the infectious agent. In a preferred aspect of the invention, the term "anti-infective agent" covers agents that are capable of killing, inhibiting or otherwise slowing the growth of the infectious agent when administered to a subject in amounts that do not exceed 50 mg/l. Preferably, the infectious agent is administered to a subject in amounts that do not exceed 20 mg/l. The term "anti-infective agent" thus covers agents that exhibit a MIC value of equal to or less than 20 μg/ml when determined as described in the examples herein. The term "anti-infective agent" may be used interchangeably with the term "antibiotic" or "anti-viral agent" or "anti-fungal agent" depending on the nature of the infectious agent. Specific examples of antibiotics commonly used for treating bacterial and fungal infections include, but is not limited to, aminoglycosides, such as amikacin, gentamicin, kanamycin, neomycin, netilmicin, streptomycin and tobramycin; cabecephems, such as loracarbef; carbapenems, such as ertapenem, imipenem/cilastatin and meropenem; cephalosporins, such as cefadroxil, cefazolin, cephalexin, cefaclor, cefamandole, cephalexin, cefoxitin, cefprozil, cefuroxime, cefixime, cefdinir, cefditoren, cefoperazone, cefotaxime, cefpodoxime, ceftazidime, ceftibuten, ceftizoxime, ceftriaxone and cefepime; macrolides, such as azithromycin, clarithromycin, dirithromycin, erythromycin and troleandomycin; monobactam; penicillins, such as amoxicillin, ampicillin, carbenicillin, cloxacillin, dicloxacillin, nafcillin, oxacillin, penicillin G, penicillin V, piperacillin and ticarcillin; polypeptides, such as bacitracin, colistin and polymyxin B; quinolones, such as ciprofloxacin, enoxacin, gatifloxacin, levofloxacin, lomefloxacin, moxifloxacin, norfloxacin, ofloxacin and trovafloxacin; sulfonamides, such as mafenide, sulfacetamide, sulfamethizole, sulfasalazine, sulfisoxazole and trimethoprim-sulfamethoxazole; tetracyclines, such as demeclocycline, doxycycline, minocycline, oxytetracycline and tetracycline;

In the present context, the term "chemosensitising compound" covers compounds that has a synergistic effect in killing, inhibiting or otherwise slowing the growth of the infectious agent when used together with, or in combination with, an anti-infective agent. When used in this context, the terms "together with" and "in combination with" should not be interpreted narrowly in the sense that the chemosensitising compound and the anti-infective agent should necessarily be administered simultaneously and/or form part of the same pharmaceutical composition, although this is one embodiment of the present invention. A synergistic effect according to this invention is obtained if the fractional Inhibitory Concentration (FIC) indices less than 0.5. The Fractional Inhibitory Concentration (FIC) index is calculated for each compound as described in WO2005/105145.

Specific examples of anti-viral agents commonly used for treating viral infections include, but is not limited to, acyclovir, amantadine, cidofovir famciclovir, fomivirsen, foscarnet, ganciclovir, interferon alpha, oseltamivir, penciclovir, ribavirin, rimantadine, trifluridine, valacyclovir, valganciclovir, vidarabine and zanamivir.

Specific examples of anti-fungal agents commonly used for treating severe fungal infections include, but is not limited to, amphotericin B, caspofungin, fluconazole, flucytosine, itraconazole, ketoconazole and voriconazole.

In the present context, an infectious agent is said to be "resistant" or "drug resistant" if the infectious agent has undergone a change which reduces or eliminates the effectiveness of an anti-infective agent which is normally used to cure infections caused by the infectious agent. Analogously, the term "drug resistance" means a circumstance when a disease, e.g. an infectious disease, does not respond to a therapeutic agent, such as an anti-infective agent. Drug resistance can be intrinsic, which means that the disease has never been responsive to the therapeutic agent, or acquired, which means that the disease ceases responding to the therapeutic agent to which the disease had previously been responsive.

In the present context, an infectious agent is said to be "multidrug resistant" if the infectious agent has undergone a change which reduces or eliminates the effectiveness of two or more anti-infective agents which are normally used to cure infections caused by the infectious agent. Analogously, "multidrug resistance" is a type of drug resistance wherein a disease, e.g. an infectious disease, is resistant to a variety of drugs, such as a variety of anti-infective agents.

The term "clinically relevant amount" is intended to mean that the anti-infective agent is administered to a patient in an amount, which, on the one hand, is capable of reducing the symptoms of the infectious disease or curing the infectious disease for which the patient is treated, but, on the other hand, is not toxic to the patient and does not lead to unacceptable side effects. As indicated above, many, if not all, of the anti-infective agents described herein are known to cause severe side effects in patients when administered in too high concentrations, i.e. in amounts which are not "clinically relevant". In the present context, the term "naturally occurring" when used in connection with the term "infectious agent", i.e. in connection with pathogenic microorganisms, means that the infectious agent giving rise to the infectious disease is a microorganism that can be found in nature, including in human beings. It will be understood that infectious agents, such as gen-manipulated laboratory strains, or infectious agents which by other means have been changed and/or manipulated by human intervention, are not considered to be covered by the term "naturally occurring".

The term "serum" is used in its normal meaning, i.e. as blood plasma without fibrinogen and other clotting factors.

Herein, the term "steady state serum concentration" (of a anti-infective agent) is defined as those values of free non-bound drug that recur with each dose and represent a state of equilibrium between the amount of anti-infective agent administered and the amount being eliminated in a given time interval. The term "steady state serum concentration" is thus intended to mean the concentration of free unbound compound (anti-infective agent) in serum. That means that the concentration is determined excluding compound which is bound to constituents of the serum (e.g. proteins).

In the present context, the term "treatment" refers to the administration of a drug to a subject and includes i) preventing an infectious disease (i.e. causing the clinical symptoms of the infectious disease not to develop), ii) inhibiting an infectious disease (i.e. arresting the development of the clinical symptoms of the infectious disease) and iii) relieving the disease (i.e. causing regression of the clinical symptoms of the infectious disease) as well as combinations thereof.

The terms "prophylaxis" or "prophylactic treatment" refers to the treatment of a subject who is not yet infected, but who may be susceptible to, or at risk of getting an infection.

The term "subject", as used herein, means a living vertebrate animal, e.g., a mammal, such as a human being.

"Pharmaceutically acceptable" means suitable for use in a mammal, in particular suitable for use in a human being.

Anti-Infective Agents

Concerning the general formulas above, the substituent's $R_1, R_2, R_3, R_4, R_5, R_6, R_7, R_8, R_{11}, R_{12}, R_{14}$ and $R_{15}$ are each individually selected from the group consisting of hydrogen, halogen, hydroxy, amino, nitro, optionally substituted $C_{1-6}$-alkyl, optionally substituted $C_{2-6}$-alkenyl, optionally substituted $C_{2-6}$-alkynyl and optionally substituted $C_{1-6}$-alkoxy, optionally substituted $C_{2-6}$-alkenyloxy, carboxy, optionally substituted $C_{1-6}$-alkoxycarbonyl, optionally substituted $C_{1-6}$-alkylcarbonyl, fomyl, optionally substituted $C_{1-6}$-alkylsulphonylamino, optionally substituted aryl, optionally substituted aryloxycarbonyl, optionally substituted aryloxy, optionally substituted arylcarbonyl, optionally substituted arylamino, arylsulphonylamino, optionally substituted heteroaryl, optionally substituted heteroaryloxycarbonyl, optionally substituted heteroaryloxy, optionally substituted heteroarylcarbonyl, optionally substituted heteroarylamino, heteroarylsulphonylamino, optionally substituted heterocyclyl, optionally substituted heterocyclyloxycarbonyl, optionally substituted heterocyclyloxy, optionally substituted heterocyclylcarbonyl, optionally substituted heterocyclylamino, heterocyclylsulphonylamino, mono- and di($C_{1-6}$-alkyl)amino, carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, amino-$C_{1-6}$-alkyl-carbonylamino, mono- and di($C_{1-6}$-alkyl)amino-$C_{1-6}$-alkyl-carbonylamino, amino-$C_{1-6}$-alkyl-amino, mono- and di($C_{1-6}$-alkyl)amino-$C_{1-6}$-alkyl-amino, cyano, guanidino, carbamido, $C_{1-6}$-alkanoyloxy, $C_{1-6}$-alkylsulphonyl, $C_{1-6}$-alkylsulphinyl, $C_{1-6}$-alkylsulphonyloxy, aminosulfonyl, mono- and di($C_{1-6}$-alkyl)aminosulfonyl, and optionally substituted $C_{1-6}$-alkylthio.

$R_{13}$ is hydrogen, halogen, hydroxy, amino, nitro, optionally substituted $C_{1-6}$-alkyl or optionally substituted $C_{1-6}$-alkoxy.

Preferably, $R_{13}$ is selected from the group consisting of hydrogen, halogen, hydroxy, amino, nitro, and optionally substituted $C_{1-6}$-alkyl. More preferably $R_{13}$ is hydrogen, hydroxy, amino, nitro, halogen, $CH_2Y$, $CHY_2$ and $CY_3$, wherein each Y is individually selected among hydrogen, hydroxy, amino, nitro or halogen.

In a preferred embodiment of the invention, $R_{13}$ is selected from the group consisting of hydrogen, $CH_3$ and $CH_2OH$.

In a more preferred embodiment of the invention, $R_{13}$ is selected from the group consisting of hydrogen and $CH_3$.

In a most preferred embodiment $R_{13}$ is hydrogen.

In a preferred embodiment of the invention, the $R_2$ substituent is an electron-withdrawing group, such as halogen, nitro or halogen-substituted $C_{1-6}$-alkyl. More preferably, $R_2$ is selected from the group consisting of F, Cl, Br, I, $CH_2Y$, $CHY_2$ and $CY_3$ (wherein Y represents a halogen atom), such as $CH_2Cl$, $CH_2F$, $CHCl_2$, $CHF_2$, $CCl_3$ or $CF_3$, in particular $CCl_3$ or $CF_3$. Most preferably, $R_2$ is $C_1$ or $CF_3$.

The substituents $R_1$, $R_3$, $R_4$, $R_5$, $R_6$, $R_7$, $R_8$, $R_{11}$, $R_{12}$, $R_{14}$ and $R_{15}$ are preferably each individually selected from the group consisting of hydrogen, optionally substituted $C_{1-6}$-alkyl and optionally substituted $C_{1-6}$-alkoxy. More preferably, all of $R_1$, $R_3$, $R_4$, $R_5$, $R_6$, $R_7$, $R_8$, $R_{11}$, $R_{12}$, $R_{14}$ and $R_{15}$ are hydrogen.

Accordingly, in a highly preferred embodiment of the invention, $R_2$ is $C_1$ or $CF_3$ and each of $R_1$, $R_3$, $R_4$, $R_5$, $R_6$, $R_7$, $R_8$, $R_{11}$, $R_{12}$, $R_{14}$ and $R_{15}$ are hydrogen.

As mentioned above, V is selected from the group consisting of S, $SO_2$, SO, 0 and NH, such as S or SO. In a highly preferred embodiment of the invention, V is S.

As will be understood, in case W is N—$(CHX)_m$—$CX(R_9)(R_{10})$ or W is N—$(CHX)_{m-1}$—CH=$C(R_9)(R_{10})$, and V is S, the anti-infective agent of the general formula (I) is a phenothiazine derivate. Thus the compound according to the invention in one aspect is a phenothiazine derivate of the general formula (III):

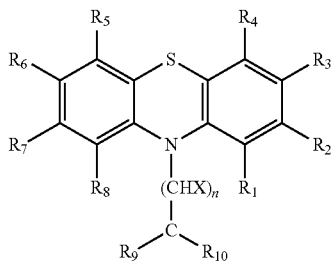

wherein m is an integer in the range of from 2 to 6, such as 2, 3, 4, 5 or 6, and each X is individually selected from the group consisting of hydrogen, halogen, hydroxy, amino, nitro, optionally substituted $C_{1-6}$-alkyl and optionally substituted $C_{1-6}$-alkoxy.

In a preferred embodiment of the invention, n is 2 or 3, X is hydrogen or $CH_3$ and $R_{12}$ is hydrogen or $CH_3$. Particularly, when n is 2, and each X is hydrogen and $R_{12}$ is hydrogen or $CH_3$, the agents of the general formula (III) show a potent anti-infective activity. Thus, in a preferred embodiment of the invention, W together with the functional group attached thereto form an alkyl chain (N—$(CHX)_n$—) with an optionally substituted heterocyclyl group. The heterocyclyl group is preferably unsubstituted or substituted in the para position ($R_{13}$). In a preferred embodiment W together with the functional group attached thereto is N—$(CH_2)_{3-4}$-methyl-piperidinyl, N—$CH_2$—$CH(CH_3)$-4-methyl-piperidinyl, N—$(CH_2)_3$-piperidinyl or N—$CH_2$—$CH(CH_3)$-4-methyl-piperidinyl. In particular, the structure where W together with the functional group attached thereto is N—$(CH_2)_3$-piperidinyl is preferred.

Specific examples of the above-mentioned phenothiazine derivatives include derivatives of perphenazine and prochlorperazine.

As will also be understood, in case W is C=CH—$(CHX)_n$—$CX(R_9)(R_{10})$ or W is C=CH—$(CHX)_{n-1}$—CH=$C(R_9)(R_{10})$ and V is S, the compound of the general formula (I) becomes a thioxanthene of the general formula (IV)

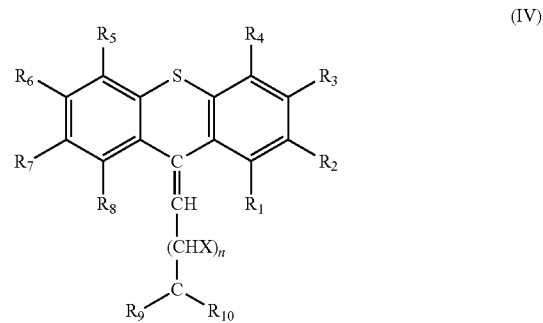

A phenothiazine of the general formulae (III) and a thioxanthene of the general formula (IV) gives rise to cis and trans isomerism. In the present context, compounds of the general formula (IVa) are said to be in the cis configuration, whereas compounds of the general formula (IVb) are said to be in the trans configuration:

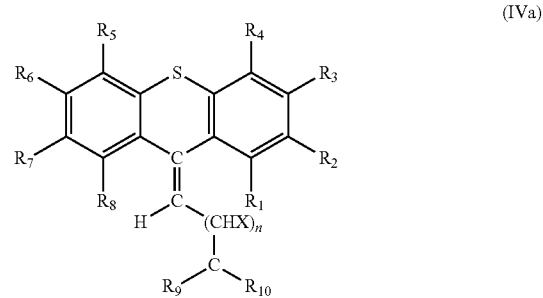

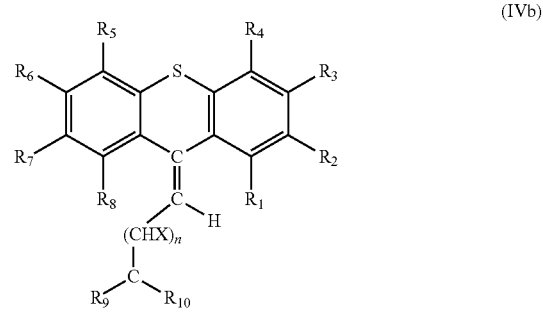

wherein n is an integer in the range of from 1 to 5, such as 1, 2, 3, 4, or 5, and each X is individually selected from the group consisting of hydrogen, halogen, hydroxy, amino, nitro, optionally substituted $C_{1-6}$-alkyl and optionally substituted $C_{1-6}$-alkoxy. $R_9$ and $R_{10}$ are each independently selected from the group consisting of hydrogen, optionally substituted $C_{1-6}$-alkyl, optionally substituted $C_{2-6}$-alkenyl, optionally substituted $C_{2-6}$-alkynyl, optionally substituted $C_{1-6}$-alkoxycarbonyl, optionally substituted $C_{1-6}$-alkylcarbonyl, optionally substituted aryl, optionally substituted aryloxycarbonyl, optionally substituted arylcarbonyl, optionally substituted heteroaryl, optionally substituted heteroaryloxycarbonyl, optionally substituted heteroarylcarbonyl, aminocarbonyl, mono- and di($C_{1-6}$-alkyl)aminocarbonyl;

or $R_9$ and $R_{10}$ together with the carbon atom to which they are attached form an optionally substituted aryl group, cycloalkyl group or heterocyclyl group, preferably an optionally substituted $C_{3-6}$-cycloalkyl, or $C_{3-6}$-heterocyclyl, preferably a nitrogen-containing heteroaryl or an optionally substituted nitrogen-containing heterocyclyl;

It is generally preferred that the compounds of the invention have the trans configuration, i.e. the structure illustrated in the general formula (IVb).

In a preferred embodiment, X is hydrogen and n is 3 to 5, in particular 3 or 4. Thus, in a preferred embodiment of the invention, W has the structure C=CH—(CH$_2$)$_2$—CX(R$_{10}$)(R$_{11}$). In another embodiment of the invention, W has the structure C=CH—(CH$_2$)$_3$—CX(R$_{10}$)(R$_{11}$). In another embodiment of the invention, W has the structure C=CH—(CH$_2$)$_4$—CX(R$_{10}$)(R$_{11}$). In another embodiment of the invention, W has the structure C=CH—CH$_2$—CH=C(R$_{10}$)(R$_{11}$). In another embodiment of the invention, W has the structure C=CH—(CH$_2$)$_2$—CH=C(R$_{10}$)(R$_{11}$). In another embodiment of the invention, W has the structure C=CH—(CH$_2$)$_3$—CH=C(R$_{10}$)(R$_{11}$).

In one interesting embodiment of the invention, R$_9$ and R$_{10}$ are each individually selected from the group consisting of hydrogen and optionally substituted C$_{1-6}$-alkyl. According to this embodiment, it is preferred that both of R$_9$ and R$_{10}$ are optionally substituted C$_{1-6}$-alkyl. Most preferably both of R$_9$ and R$_{10}$ are CH$_3$.

In another interesting embodiment of the invention, R$_9$ and R$_{10}$, together with the carbon atom to which they are attached, form an optionally substituted aryl, an optionally substituted C$_{3-6}$-cycloalkyl or a heterocyclyl, such as optionally substituted 2-pyrrolinyl, optionally substituted 3-pyrrolinyl, optionally substituted pyrrolidinyl, optionally substituted 2-imidazolinyl, optionally substituted imidazolidinyl, optionally substituted 2-pyrazolinyl, optionally substituted 3-pyrazolinyl, optionally substituted pyrazolidinyl, optionally substituted piperidinyl, optionally substituted morpholinyl, optionally substituted thiomorpholinyl or optionally substituted piperidinyl. Preferably R$_9$ and R$_{10}$ together with the carbon atom to which they are attached form an optionally substituted nitrogen-containing heteroaryl or an optionally substituted nitrogen-containing heterocyclyl wherein the nitrogen atom is separated by two carbon atoms from the carbon atom to which R$_9$ and R$_{10}$ are attached. According to this embodiment, it is preferred that R$_9$ and R$_{10}$, together with the carbon atom to which they are attached, form an optionally substituted piperidinyl or an optionally substituted piperazinyl, in particular an optionally substituted piperidinyl. The piperidinyl ring may be unsubstituted, but is preferably substituted with an optionally substituted C$_{1-6}$ alkyl group, in particular in the para position, i.e. an optionally substituted C$_{1-6}$ alkyl group is covalently attached to the nitrogen atom of the piperidinyl ring. In a highly preferred embodiment of the invention, the optionally substituted C$_{1-6}$-alkyl is selected from the group consisting of —CH$_3$, —CH$_2$OH, —CH$_2$—CH$_3$ and CH$_2$—CH$_2$OH, such as —CH$_3$ or —CH$_2$—CH$_2$OH, in particular —CH$_2$—CH$_2$OH.

As is evident from the formulae shown herein and the definitions associated therewith, certain of the compounds described herein are chiral. Moreover, the presence of certain unsaturated or cyclic fragments or multiple stereogenic atoms provides for the existence of diastereomeric forms of some of the chemosensitising compounds. The invention is intended to include all stereoisomers, including optical isomers, and mixtures thereof, as well as pure, partially enriched, or, where relevant, racemic forms. In particular, many of the chemosensitising compounds described herein may be in the form of E- or Z-stereoisomers, or mixtures of such isomers.

In a preferred embodiment of the invention W is C=CH—(CHX)$_n$—CX(R$_9$)(R$_{10}$) or W is C=CH—(CHX)$_{n-1}$—CH=C(R$_9$)(R$_{10}$), and in these embodiment it is preferred that n is 2 or 3 or 4. Furthermore, it is preferred that X is hydrogen or CH$_3$. It is also preferred in this embodiment that R$_9$ and R$_{10}$, together with the carbon atom to which they are attached form an optionally substituted aryl. In a preferred embodiment R$_9$ and R$_{10}$, together with the carbon atom to which they are attached form an optionally substituted C$_{3-6}$-cycloalkyl or an optionally substituted C$_{3-6}$-heterocyclyl. Preferably, R$_9$ and R$_{10}$, together with the carbon atom to which they are attached form an optionally substituted C$_6$-cycloalkyl or an optionally substituted C$_6$-heterocyclyl.

In a preferred embodiment, R$_{13}$ is hydrogen or CH$_3$. Particularly, it has been shown that when n is 2, and each X is hydrogen and R$_{13}$ is hydrogen or CH$_3$, the agents of the general formula (IVa) and (IVb) show a potent anti-infective activity at clinically relevant concentrations. Thus in a preferred embodiment of the invention, W together with the functional group attached thereto form an alkenyl chain (C=C—(CHX)$_n$—) with an optionally substituted piperidinyl group. The piperidinyl group is preferably unsubstituted or substituted in the para position (R$_{13}$). Thus, in a preferred embodiment W together with the functional group attached thereto is CCH—(CH$_2$)$_2$-4-methyl-piperidinyl, CCH—CH$_2$—CH(CH$_3$)-4-methyl-piperidinyl, CCH—(CH$_2$)$_2$-piperidinyl or CCH—CH$_2$—CH(CH$_3$)— piperidinyl. In particular, the structure where W together with the functional group attached thereto is CCH—(CH$_2$)$_2$-4-methyl-piperidinyl is preferred.

Surprisingly, the thioxanthene anti-infective agents of the present invention are increasingly efficient as anti-infective agents with increasing degree of isomeric purity. In other words, it has surprisingly been shown that while both the agents of the general formula (IVa) (cis-isomers) and the agents of the general formula (IVb) (trans-isomers) display potent anti-infective properties, the isomeric mixtures of the agents of the general formula (IVa) and (IVb) show a reduced anti-infective activity.

Particularly, the presence of the trans-isomer inhibits the anti-infective properties of the cis-isomer and that presence of the cis-isomer inhibits the anti-infective properties of the trans-isomer. Even small amounts of isomeric impurity of one isomer may inhibit the anti-infective properties of the other relevant anti-infective isomer.

Consequently, it is generally preferred that the compounds of the general formula (III) are used as pure or substantially pure isomers. Accordingly, the compounds according to this embodiment are preferably used in an isomeric purity of at least 60% such as at least 70%, such as at least 80%, such as at least 90% or even at least 95%, or even at least 98%.

It has been shown during the course of the experiments leading to the present invention that the trans-forms of the compounds according to the invention are the most potent anti-infective agents. Further, the apparent lack of anti-psychotic activity or extrapyramidal side effects of the trans-forms makes them particularly attractive for use as anti-infective agents. Accordingly, it is generally preferred that the compounds of the general formula (IV) have the trans configuration, i.e. the structure shown in the general formula (IVb).

It should furthermore be understood that the anti-infective agents described herein include possible salts thereof, of which pharmaceutically acceptable salts are of course especially relevant for the therapeutic applications. Salts include acid addition salts and basic salts. Examples of acid addition salts are hydrochloride salts, fumarate, oxalate, etc. Examples of basic salts are salts where the (remaining) counter ion is selected from alkali metals, such as sodium and potassium, alkaline earth metals, such as calcium salts, potassium salts, and ammonium ions ($^+$N(R')$_4$, where the R's independently designate optionally substituted C$_{1-6}$-alkyl, optionally substituted $C_{2-6}$-alkenyl, optionally substituted aryl, or optionally substituted heteroaryl). Pharmaceutically acceptable salts are, e.g., those described in Remington's—The Science and Practice of Pharmacy, 20th Ed. Alfonso R. Gennaro (Ed.), Lippincott, Williams & Wilkins; ISBN: 0683306472, 2000, and in Encyclopedia of Pharmaceutical Technology.

The effect of the anti-infective agents may be assayed as described herein and the efficiency of the anti-infective agent against selected microorganisms may be expressed as the MIC value.

The Minimal Inhibitory Concentration, (MIC) is defined as the lowest inhibitory concentration showing no visible growth according to the NCCLS Guidelines.

The anti-infectivity of the anti infective agents described herein, may be assessed by any of the methods available to those skilled in the art, including the in vitro assays described in the examples herein. In a preferred embodiment of the invention, the anti-infective agent and the infectious agent (and hence the infectious disease to be treated) exhibit a MIC value of equal to or less than 50 μg/ml and preferably less than 20 μg/ml when determined as described in the examples herein. More preferably the anti-infective agent and the infectious agent exhibit a MIC value of equal to or less than 16 μg/ml when determined as described in the examples herein. Even more preferably, the MIC value is equal to or less than 8 μg/ml, such as equal to or less than 4 μg/ml, e.g. at the most 4.0. Even more preferably, the MIC value is equal to or less than 2 μg/ml, such as at the most 2.0, at the most 1.0 or even at the most 0.5.

Therapy, Pharmaceutical Compositions and Dosages

As explained above, the anti-infective agents described herein are useful for the treatment of infectious diseases. Thus, the anti-infective agents described herein may be used for the manufacture of a medicament for the treatment of an infectious disease, wherein the anti-infective agents are the sole anti-infective agent.

The compounds disclosed may also be used in combination with other anti-infective agents.

Thus, in one embodiment the invention relates to the anti-infective agents described herein for use in treatment of an infectious disease, wherein the anti-infective agents are the sole anti-infective agent.

In addition, the anti-infective agents described herein are useful for prophylactic treatment of infectious diseases. This may be particularly relevant in situations where a person has a high risk of getting infections, such as immuno-suppressed patients or patients undergoing surgery. Thus, the anti-infective agents described herein may also be used for the manufacture of a medicament for the prophylactic treatment of an infectious disease, wherein the anti-infective agents are the sole anti-infective agent.

Thus, in another embodiment the invention relates to the anti-infective agents described herein for use in prophylactic treatment of an infectious disease, wherein the anti-infective agents are the sole anti-infective agent.

In a further aspect, the present invention is directed to the anti-infective agents described herein for use as medicaments for the treatment of infectious disease.

In a further aspect, the present invention is directed to the anti-infective agents described herein for use as medicaments for the treatment of multidrug resistant infections.

In a further aspect, the present invention is directed to the anti-infective agents described herein for use (e.g. as medicaments) for inhibiting the development of antibiotic resistance in an infectious agent.

A further aspect of the present invention relates to a method for treating or preventing an infectious disease in a subject, said method comprising administering to said subject an anti-infective agent as described herein.

The compounds according to the invention have been shown to have a synergistic effect when used in combination with other anti-bacterial agents. Thus, the compounds according to the invention may also be used as chemosensitising compounds.

The effect of the chemosensitising compounds (which is believed to be caused by reversing drug resistance or multiple drug resistance) may be assayed as described herein and the efficiency of the chemosensitising compound in combination with selected anti-infective agents against selected microorganisms may be expressed as the DR ratio and/or the FIC index.

The Drug Resistance (DR) ratio is defined as the ratio between the MIC value for anti-infective agent alone divided by the MIC for the anti-infective agent in the presence of the chemosensitising compound. This ratio represents the increase in apparent potency of the anti-infective agent caused by the chemosensitising compound, and may be expressed as $$\text{DR ratio} = (\text{MIC}_{anti\text{-}infective\ agent}) / (\text{MIC}_{anti\text{-}infective\ agent + chemosensitising\ compound})$$

The Fractional Inhibitory Concentration (FIC) index may be calculated for each anti-infective agent alone and in combination with chemosensitising according to the following formulae:

$$\text{FIC} = \text{FIC}_{chemosensitising\ compound} + \text{FIC}_{anti\text{-}infective\ agent}$$

where:

$$\text{FIC}_{chemosensitising\ compound} = (\text{MIC}_{chemosensitising\ compound + anti\text{-}infective\ agent}) / (\text{MIC}_{chemosensitising\ compound})$$

$$\text{FIC}_{anti\text{-}infective\ agent} = (\text{MIC}_{anti\text{-}infective\ agent + chemosensitising\ compound}) / (\text{MIC}_{anti\text{-}infective\ agent})$$

The synergistic effects of the chemosensitising compounds described herein, i.e. their ability to reverse drug resistance or multiple drug resistance in a microorganism, may be assessed by any of the methods available to those skilled in the art, including the in vitro assays described in the examples herein. In a preferred embodiment of the invention, the chemosensitising compound, the anti-infective agent and the infectious agent (and hence the infectious disease to be treated) exhibit a FIC index of at the most 0.5 when determined as described in the examples herein. More preferably, the FIC index is at the most 0.4, such as at the most 0.3.

For chemosensitising compounds, which are effective inhibitors, this means that the ratio $(\text{MIC}_{chemosensitising\ compound + anti\text{-}infective\ agent}) / (\text{MIC}_{chemosensitising\ compound})$ becomes close to zero, which, in turn, means that $\text{FIC}_{chemosensitising\ compound} \approx 0$. This also means that $\text{FIC} \approx \text{FIC}_{anti\text{-}infective\ agent} = (\text{MIC}_{anti\text{-}infective\ agent + chemosensitising\ compound}) / (\text{MIC}_{anti\text{-}infective\ agent}) \approx 1/\text{DR}$.

Accordingly, in another preferred embodiment of the invention, the compound according to the invention and the infectious agent (and hence the infectious disease to be treated) exhibit a DR ratio of at least 2. More preferably, the DR ratio is at least 5, such as at least 10, e.g. at least 20. Even more preferably, the MIC value is at least 30, such as at least 50, at least 75 or even at least 100.

Therapy

As will be understood from the disclosure herein, the infectious disease to be treated is normally caused by an infectious agent, such as a bacterium, a virus, a fungi or an intra- or extra-cellular parasite, in particular a bacterium. The infectious agent is typically naturally-occurring, i.e. a naturally-occurring bacterium, a naturally occurring virus, a naturally occurring fungi or a naturally occurring intra- or extra-cellular parasite, in particular a naturally-occurring bacterium.

More particularly, the infectious agent may be Gram negative or Gram positive bacteria.

Specific examples include Gram negative bacteria of a genus selected from the group consisting of *Escherichia, Proteus, Salmonella, Klebsiella, Providencia, Enterobacter, Burkholderia, Pseudomonas, Acinetobacter, Aeromonas, Haemophilus, Yersinia, Neisseria, Erwinia, Rhodopseudomonas* and *Burkholderia*.

Specific examples of Gram positive bacteria include bacteria from a genus selected from the group consisting of *Lactobacillus, Azorhizobium, Streptococcus, Pediococcus, Photobacterium, Bacillus, Enterococcus, Staphylococcus, Clostridium, Butyrivibrio, Sphingomonas, Rhodococcus* and *Streptomyces*.

In other embodiments, the infectious agent is, e.g., from a genus selected from the group consisting of *Methanobacierium, Sulfolobus, Archaeoglobu, Rhodobacter* and *Sinorhizobium*.

In other embodiments, the infectious agent is, e.g., an acid-fast bacteria of the *Mycobacterium* species, such as *Mycobacterium tuberculosis, Mycobacterium bovis. Mycobacterium avium* and *Mycobacterium leprae*, along with members of a related genus *Nocardia* such as *Nocardia asteroides, Nocardia brasiliensis* and *Nocardia caviae*.

In still other embodiments, the infectious agent is fungi, such as from the genus *Mucor* or *Candida*, e.g., *Mucor racemosus* or *Candida albicans*; from genus *Crytococcus* e.g., *Cr. Neoformans*; or from Genus *Aspergillus*, e.g., *A. fumingatus*.

In yet other embodiments, the infectious agent is protozoa, such as a malaria or cryptosporidium parasite.

Toxicity and therapeutic efficacy of the anti-infective agents described herein can be determined by standard pharmaceutical procedures in cell cultures or experimental animals, e.g., by determining the $LD_{50}$ (the dose lethal for 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$ ($LD_{50}/ED_{50}$). Anti-infective agents which exhibit large therapeutic indices are preferred. The data obtained from these cell culture assays or animal studies can be used in formulating a range of dosage for use in human subjects. The dosage of such anti-infective agents lies preferably within a range of circulating concentrations that include the $ED_{50}$ with little or no toxicity. The dosage may vary within this range depending upon the dosage form employed and the route of administration utilised.

Pharmaceutical Compositions

The anti-infective agents described herein are typically formulated in a pharmaceutical composition prior to use as a drug substance.

Accordingly, in a further aspect the present invention relates to a pharmaceutical composition comprising an anti-infective agent as described herein and at least one pharmaceutically acceptable carrier or exipient.

The administration route of the anti-infective agents described herein may be any suitable route that leads to a concentration in the blood or tissue corresponding to a clinically relevant concentration. Thus, e.g., the following administration routes may be applicable although the invention is not limited thereto: the oral route, the parenteral route, the cutaneous route, the nasal route, the rectal route, the vaginal route and the ocular route. It should be clear to a person skilled in the art that the administration route is dependant on the particular anti-infective agent in question, particularly, the choice of administration route depends on the physicochemical properties of the anti-infective agent together with the age and weight of the patient and on the particular disease or condition and the severity of the same. In general, however, the oral and the parental routes are preferred.

The anti-infective agents described herein may be contained in any appropriate amount in the pharmaceutical composition, and are generally contained in an amount of about 0.1-95% by weight of the total weight of the composition. The composition may be presented in a dosage form, such as a unit dosage form, which is suitable for the oral, parenteral, rectal, cutaneous, nasal, vaginal and/or ocular administration route. Thus, the composition may be in form of, e.g., tablets, capsules, pills, powders, granulates, suspensions, emulsions, solutions, gels including hydrogels, pastes, ointments, creams, plasters, drenches, delivery devices, suppositories, enemas, injectables, implants, sprays, aerosols and in other suitable form.

The pharmaceutical compositions may be formulated according to conventional pharmaceutical practice, see, e.g., "Remington's Pharmaceutical Sciences" and "Encyclopedia of Pharmaceutical Technology", edited by Swarbrick, J. & J. C. Boylan, Marcel Dekker, Inc., New York, 1988. Typically, the anti-infective agents described herein are formulated with (at least) a pharmaceutically acceptable carrier or exipient. Pharmaceutically acceptable carriers or exipients are those known by the person skilled in the art.

Pharmaceutical compositions for oral use include tablets which contain an anti-infective agent as described herein, optionally in combination with at least one further anti-infective agent, in admixture with non-toxic pharmaceutically acceptable excipients. These excipients may be, for example, inert diluents or fillers, such as sucrose, sorbitol, sugar, mannitol, microcrystalline cellulose, starches including potato starch, calcium carbonate, sodium chloride, lactose, calcium phosphate, calcium sulfate or sodium phosphate; granulating and disintegrating agents, for example, cellulose derivatives including microcrystalline cellulose, starches including potato starch, croscarmellose sodium, alginates or alginic acid; binding agents, for example, sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone or polyethylene glycol; and lubricating agents, including glidants and antiadhesives, for example, magnesium stearate, zinc stearate, stearic acid, silicas, hydrogenated vegetable oils or talc.

Other pharmaceutically acceptable excipients can be colorants, flavouring agents, plasticisers, humectants, buffering agents, etc.

The tablets may be uncoated or they may be coated by known techniques, optionally to delay disintegration and absorption in the gastrointestinal tract and thereby providing a sustained action over a longer period. The coating may be adapted to release the anti-infective agent in a predetermined pattern, e.g., in order to achieve a controlled release formulation (see below) or it may be adapted not to release the active drug substance until after passage of the stomach (enteric coating). The coating may be a sugar coating, a film coating (e.g. based on hydroxypropyl methylcellulose, methylcellulose, methyl hydroxyethylcellulose, hydroxypropylcellulose, carboxymethylcellulose, acrylate copolymers (Eudragit E®), polyethylene glycols and/or polyvinylpyrrolidone) or an enteric coating (e.g. based on methacrylic acid copolymer (Eudragit® L and S), cellulose acetate phthalate, hydroxypropyl methylcellulose phthalate, hydroxypropyl methylcellulose acetate succinate, polyvinyl acetate phthalate, shellac and/or ethylcellulose).

Furthermore, a time delay material such as, e.g., glyceryl monostearate or glyceryl distearate may be employed.

In addition, the solid tablet compositions as mentioned above may be provided with a coating adapted to protect the composition from unwanted chemical changes, e.g. chemical degradation, prior to the release of the anti-infective agent.

The coating may be applied on the solid dosage form in a similar manner as that described in "Aqueous film coating" by James A. Seitz in "Encyclopedia of Pharmaceutical Technology", Vol 1, pp. 337-349 edited by Swarbrick, J. & J. C. Boylan, Marcel Dekker, Inc., New York, 1988.

Formulations for oral use may also be presented as chewing tablets, or as hard gelatin capsules wherein the active ingredient is mixed with an inert solid diluent, for example, potato starch, lactose, microcrystalline cellulose, calcium carbonate, calcium phosphate or kaolin, or as soft gelatin capsules wherein the active ingredient is mixed with water or an oil medium, for example, peanut oil, liquid paraffin, or olive oil.

Powders and granulates may be prepared using the ingredients mentioned above under tablets and capsules in a conventional manner using, e.g., a mixer, a fluid bed apparatus or a spray drying equipment.

Controlled release compositions for oral use may, e.g., be constructed to release the active drug substance by controlling the dissolution and/or the diffusion of the active drug substance.

Dissolution or diffusion controlled release can be achieved by appropriate coating of a tablet, capsule, pellet or granulate formulation of the anti-infective agent, or by incorporating the anti-infective agent in question in, e.g., an appropriate matrix.

A controlled release coating may comprise one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methyl-methacrylate, 2-hydroxymethacrylate, methacrylate hydrogels, 1,3-butylene glycol, ethylene glycol methacrylate and/or polyethylene glycols.

In a controlled release matrix formulation of the anti-infective agent, the matrix material may comprise, e.g., hydrated methylcellulose, carnauba wax and stearyl alcohol, carbopol 934, silicone, glyceryl tristearate, methyl acrylate-methyl methacrylate, polyvinyl chloride, polyethylene and/or halogenated fluorocarbon.

A controlled release composition of the anti-infective agents described herein, may also be in the form of a buoyant tablet or capsule, i.e. a tablet or capsule which upon oral administration floats on top of the gastric content for a certain period of time. A buoyant tablet formulation of the anti-infective agent in question can be prepared by granulating a mixture of the anti-infective agent, excipients and 20-75% w/w of hydrocolloids, such as hydroxyethylcellulose, hydroxypropylcellulose and hydroxypropylmethylcellulose. The obtained granules can then be compressed into tablets. On contact with the gastric juice, the tablet can form a substantially water-impermeable gel barrier around its surface. This gel barrier takes part in maintaining a density of less than one, thereby allowing the tablet to remain buoyant in the gastric juice.

Powders, dispersible powders or granules suitable for preparation of an aqueous suspension by addition of water are also convenient dosage forms. Formulation as a suspension provides the anti-infective agent in admixture with a dispersing or wetting agent, suspending agent and one or more preservatives.

Suitable dispersing or wetting agents are, for example, naturally-occurring phosphatides, as e.g. lecithin, or condensation products of ethylene oxide with e.g. a fatty acid, a long chain aliphatic alcohol or a partial ester derived from fatty acids and a hexitol or a hexitol anhydrides, for example, polyoxyethylene stearate, polyoxyethylene sorbitol monooleate, polyoxyethylene sorbitan monooleate, etc.

Suitable suspending agents are, for example, sodium carboxymethylcellulose, methylcellulose, sodium alginate, etc.

The pharmaceutical composition may also be administered parenterally by injection, infusion or implantation (intravenous, intramuscular, intraarticular, subcutaneous or the like) in dosage forms, formulations or e.g. suitable delivery devices or implants containing conventional, non-toxic pharmaceutically acceptable carriers and adjuvants.

The formulation and preparation of such compositions is well-known to those skilled in the art of pharmaceutical formulation. Specific formulations can be found in the textbook entitled "Remington's Pharmaceutical Sciences".

Compositions for parenteral use may be presented in unit dosage forms, e.g. in ampoules, or in vials containing several doses and in which a suitable preservative may be added (see below). The composition may be in form of a solution, a suspension, an emulsion, an infusion device or a delivery device for implantation or it may be presented as a dry powder to be reconstituted with water or another suitable vehicle before use. Apart from the anti-infective agents described herein, the compositions may comprise suitable parenterally acceptable carriers and/or excipients or the active drug substance may be incorporated into microspheres, microcapsules, nanoparticles, liposomes or the like for controlled release. Furthermore, the composition may, in addition, conveniently comprise suspending, solubilising, stabilising, pH-adjusting agents and/or dispersing agents.

In another interesting embodiment of the invention, the pharmaceutical composition is a solid dosage form, such as a tablet, prepared from the particulate material described in WO 03/004001 and WO 2004/062643.

As indicated above, the pharmaceutical compositions may contain the anti-infective agent in the form of a sterile injection. To prepare such a composition, the anti-infective agent is dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution and isotonic sodium chloride solution. The aqueous formulation may also contain one or more preservatives, for example, methyl, ethyl or n-propyl p-hydroxybenzoate. In cases where anti-infective agent is only sparingly or slightly soluble in water, a dissolution enhancing or solubilising agent can be added or the solvent may apart from water comprise 10-60% w/w of propylene glycol or the like.

Dosages

As discussed in detail previously, an important aspect of the present invention is the realisation that the anti-infective agents described herein are capable of killing infective agents when administered in clinical relevant amounts, i.e. in amounts sufficiently small to avoid the severe side effects normally associated with the anti-infective agents described herein.

It will be understood that the dosage to be administered will be dependent on the administration form (see below). Independently, of the administration form, the anti-infective agent should be administered in clinically relevant amounts, i.e. in amounts which on the one hand exert the relevant therapeutic effect, but on the other hand does not provide severe side effects.

The anti-infective agents according to the invention may bind to several constituents in the serum, thus necessitating an increased dosage of the agent. However, too high a dosage may lead to undesired side-effects. Thus, in order to achieve the objects of the invention, a steady state serum concentration of less than 200 mg/ml, such as 150 mg/ml or 100 mg/ml or 50 mg/l, preferably 20 mg/l of free non-bound agent is appropriate. In general treatment of infections from gram negative bacteria requires higher doses than treatment of infections with gram positive bacteria. Thus, in a preferred embodiment of the invention the anti-infective agent as described herein is administered in a clinically relevant amount giving rise to a steady state serum concentration of between 0.5 to 200 mg/ml, such as between 0.5 to 150 mg/ml or between 0.5 to 100 mg/ml or between 1.0 to 50 mg/l or between 1.5 to 20 mg/l of free non-bound agent. More preferably, the anti-infective agent is administered in a relevant amount giving rise to a steady state serum concentration of less than 10 mg/l such as less than 8.0 mg/l. More preferably, the anti-infective agent is administered in a clinically relevant amount giving rise to a steady state serum concentration of less than 7.0 mg/l, such as less than 6.0 mg/l, e.g. less than 5.0 mg/l. In some cases the anti-infective agent is administered in a clinically relevant amount giving rise to a steady state serum concentration of less than 4.0 mg/l, such as less than 3.0 mg/l, e.g. less than 2.0 mg/l. In some cases the anti-infective agent is administered in a clinically relevant amount giving rise to a steady state serum concentration of less than 1.5 mg/l, e.g. about 1.0 mg/l or about 0.5 mg/l.

In other words, the anti-infective agent is preferably administered in a clinically relevant amount giving rise to a steady state serum concentration in the interval of from 0.01 µg/l to less than 200.0 mg/l, such as 0.01 µg/l to less than 150.0 mg/l, such as 0.01 µg/l to less than 100.0 mg/l, such as 0.01 µg/l to less than 50.0 mg/l such as 0.01 µg/l to less than 20.0 mg/l such as 0.01 µg/l to less than 10.0 mg/l and such as 0.01 µg/l to less than 8.0 mg/l, such as in the interval of from 0.02 µg/l to 7.0 mg/l, e.g. in the interval of from 0.04 µg/l to 6.0 mg/l. More preferably, the steady state serum concentration of the anti-infective agent is in the interval of from 0.06 µg/l to 5.0 mg/l, such as is in the interval of from 0.08 µg/l to 4.0 mg/l, e.g. in the interval of from 0.1 µg/l to 3.0 mg/l. Even more preferably, the steady state serum concentration of the anti-infective agent is in the interval of from 0.2 µg/l to 2.0 mg/l, such as in the interval of from 0.4 µg/l to 2.0 mg/l, e.g. in the interval of from 0.5 µg/l to 2.0 mg/l. Still more preferably, the steady state serum concentration of the anti-infective agent is in the interval of from 0.6 µg/l to 2.0 mg/l, such as in the interval of from 0.8 µg/l to 2.0 mg/l, e.g. in the interval of from 0.9 µg/l to 2.0 mg/l. Most preferably, the steady state serum concentration of the anti-infective agent is in the interval of from 1.0 µg/l to 2.0 mg/l, such as in the interval of from 1.5 µg/l to 2.0 mg/l, e.g. in the interval of from 1.5 µg/l to 1.5 mg/l.

The anti-infective agent is preferably administered in an amount of about 0.1 to 10.000 mg per day, such as about 0.5 to 5000 mg per day, or such as about 1.0 to 2000 mg per day, or such as about 2.0 to 1000 mg per day. As will be understood by the skilled person, the actual amount to be administered will inter alia be dependent on the administration route, i.e. whether the anti-infective agent is administered orally, intravenous, intramuscular, etc.

For compositions adapted for oral administration for systemic use, the dosage is normally 1 mg to 3 g per dose administered 1-4 times daily for 1 day to 12 months depending on the infectious disease to be treated.

For parenteral administration, in particular intravenous administration, a dose of about 0.1 to about 2000 mg per day is convenient. For intravenous administration a dose of about 0.1 to about 2000 mg per day administered for 1 day to 12 months is convenient.

The above-mentioned steady state serum concentrations and dosages will give rise to the desired clinical effects and, at the same time, avoid the severe side effects normally associated with the anti-infective agents described herein. Some of the anti-infective agents described herein, in particular the anti-infective agents of the general formula IIIb, may however be administered in higher amounts, thereby giving rise to steady state serum concentrations above the levels indicated above. This is due to the fact that these anti-infective agents are expected not to exhibit severe side effects, even when administered in higher amounts.

The invention is further illustrated by the below, non-limiting, examples.

Materials and Methods

Bacteria

Clinical isolates were obtained from the USA, Canada, Europe and Middle East, and standard control strains were obtained from the ATCC (American Type Culture Selection USA) and CCUG (Control Culture University of Göteborg, Sweden). The collection included multi resistant isolates and represents clinical important bacteria and fungi.

The resistant cells were approximately 10 to 1000 times more resistant compared to sensitive cell lines and maintained a stable drug resistance phenotype when grown in drug-free medium. All Staphylococci were typed in order to ensure that the isolates did not represent the same clone/strain.

Drugs

Drugs were dissolved in small amounts of water or 1% DMSO (final culture concentration of DMSO less than 0.05% DMSO) before dilution with medium. Solutions were freshly prepared for each experiment. The purity of the compounds was >95%.

Effect of Drugs on Microbial Cell Growth

Cell growth was tested using the Minimal Inhibitory Concentration (MIC) susceptibility tests by use of the microdilution broth method in accordance to the NCCLS Guidelines (NCCLS Guidelines, Methods for Dilution Antimicrobial Susceptibility Tests for Bacteria That Grow Aerobically; Approved Standard, Sixth Edition, Volume 23; Number 2). The minimum inhibitory concentration (MIC), is defined as the lowest concentration of drug which inhibits growth of the test organism, in the sense that no visible growth is detected (total inhibition of growth). In example 2, MIC of the compounds used on fungal microorgansims was determined from the IC90 measurements according to NCCLS Guidelines.

A log phase culture of bacteria was diluted with fresh pre-warmed Mueller-Hinton medium and adjusted to a defined OD at 600 nm in order to give a final concentration of $1 \times 10^{4-5}$ bacteria/ml medium. The bacterial culture was transferred to microtiter-plates and culture was added to each well. Drug was added to the bacterial culture in the wells as two-fold dilution series of drug in order to give final concentrations ranging from 0.03 to 128 µg/ml. Trays were incubated at 37° C. by shaking in a robot analyzer, PowerWave$_x$, software KC$^{4+}$ Kebo. Lab, Copenhagen, for 16 h and optical densities were measured at 600 nm during the incubation time in order to record growth curves. Wells containing bacterial culture without drug were used as controls to ensure correct inoculum size and bacterial growth during the incubation. Cultures were tested in order to detect contaminations. Each experiment was repeated in triplicate. MIC values represent the mean values of two separate triplicate experiments. Intra- and interassay variation was <5%.

Definition of Growth Inhibitory Effect of Anti-Infective Agents

The bacterial growth in the wells is described by the lagphase i.e. the period until (before) growth starts, the logphase i.e. the period with maximal growth rate, the steady-statephase followed by the deathphase. These parameters are used when evaluating the inhibitory effect of the drug on the bacterial growth, by comparing growth curves with and without drug.

The total inhibition of bacterial growth is defined as: OD (16 h)=OD (0 h) or no visible growth according to NCCLS Guidelines.

Inhibition 90 (IC90) is defined as: OD responding a 90% growth inhibition.

In the examples below, the compounds tested are as shown in Table 1:

TABLE 1

Test compounds 1 (N-dealkyl-transclopenthixol) and 2 (trans-clopentixol) are comparative compounds).

| No | Structure | R$_2$ | n | X$_2$ | Heterocycle |
|---|---|---|---|---|---|
| 1 | [structure] | Cl | 2 | H | piperazine |
| 2 | [structure] | Cl | 2 | CH$_2$CH$_2$OH | piperazine |
| 3 | [structure] | Cl | 2 | H | piperidine |
| 4 | [structure] | Cl | 2 | CH$_2$CH$_2$OH | Piperidine |

Example 1a

Effect on Clinically Relevant Bacterial Isolates

Conclusion: Anti-infective effect of compound 3 is superior compared to compounds 1 and 2.

Strains: All strains used are multiresistant clinical isolates including resistance against betalactam antibiotics, quinolones and aminoglycosides (MIC values>16 µg per ml). Ten strains in each test group.

TABLE 1A

Median MIC values of compounds (µg/ml), Ten strains in each test group.

| Compound | S. aureus | S. epidermidis | E. faecalis | E. faecium | E. coli |
|---|---|---|---|---|---|
| Compound 2 | 8 | 8 | 1 | 1 | 16 |
| Compound 1 | 3.6 | 2.4 | 0.6 | 0.6 | 6 |
| Compound 3 | 2 | 1 | 0.1 | 0.1 | 3 |

As seen, Compound 3 exhibits strong anti-infective activity and is superior to transclopenthixol and N-dealkyl- transclopenthixol in all of the test groups.

Example 1b

Effect on Clinically Relevant Human Isolates of Multiresistant and Susceptible Species of Staphylococci, Streptococci, Micrococci and Gram Negative Species Clinically relevant human bacterial isolates of Staphylococci, Streptococci, Micrococci and Gram negative species was cultured and assayed as described above for susceptibility towards the compounds listed in table 1b. The results are shown in Table 1b.

The results in Table 1b show that the tested compounds exhibit strong antimicrobial activity against all of the gram positive and gram negative clinical isolates including all of the multi resistant isolates. The effects of the compounds were approximately equipotent modest in both the sensitive and resistant isolates. (data not shown).

Example 2

Effect on Resistant Clinical Isolates of *Enterococcus faecalis* and *Enterococcus faecium*

Clinically relevant isolates were cultured and assayed as described above. The results are shown in Table 2.

TABLE 1b

Antimicrobial effect of dealkylated phenothiazine or thioxanthene compounds on multiresistant resistant and susceptible clinical isolates of *Staphylococci, Micrococci, Streptococci* and Gram negative species.

| Structure | $R_2$ | n | $X_2$ | Heterocycle | Micro* Organism (no: 16) | MIC µ/ml Mean |
|---|---|---|---|---|---|---|
| 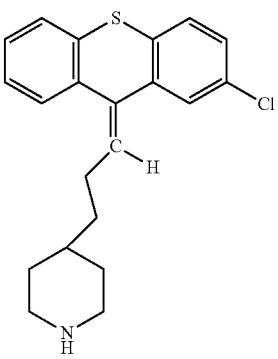 | Cl | 2 | H | piperidine | *Staphylococci, Micrococci.* Including MRSA | 0.25 |
| | | | | | *Streptococci* | 0.25 |
| | | | | | Gram negative sp. | 3 |
| 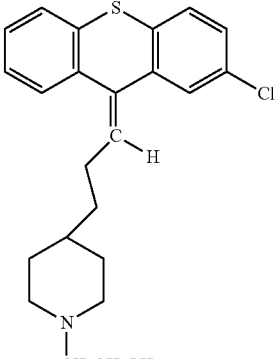 | Cl | 2 | $CH_2CH_2OH$ | piperidine | *Staphylococci, Micrococci.* Including MRSA | 1 |
| | | | | | *Streptococci* | 1 |
| | | | | | Gram negative sp. | 3 |

*Each group consists of 8 Multiresistant isolates and 8 susceptible isolates.

TABLE 2

Antimicrobial effect of dealkylated phenothiazine or thioxanthene compounds on multiresistant resistant and susceptible clinical isolates of *Enterococci* species.

| Structure | $R_2$ | n | $X_2$ | Heterocycle | Micro* Organism (no: 16) | MIC µ/ml Mean (range) |
|---|---|---|---|---|---|---|
| (thioxanthene with chloro and piperidine, NH) | Cl | 2 | H | piperidine | *Enterococci* sp. | 0.125 (0.06-0.125) |
| (thioxanthene with chloro and piperidine, N-CH₂CH₂OH) | Cl | 2 | CH$_2$CH$_2$OH | piperidine | *Enterococci* sp. | 0.5 (0.125-1.0) |

*Each group consists of 8 Multiresistant isolates representing the following resistances VanB: isolates (exhibits vanB-glycopeptideresistance which affects primarily vancomycin and not teicoplanin);. VanA (isolates exhibits vanA-glycopeptideresistance which affects both vancomycin and teicoplanin); HLAR: (isolates exhibits high level aminoglycoside resistance); BLR,CR (isolates exhibits betalactam and carbapenem resistance),. and 8 susceptible isolates The experiment shows that the tested compounds exhibit strong antimicrobial activity against resistant and multi-resistant isolates including vancomycin resistant, teicoplanin resistant and high level aminoglycoside resistant *Enterococcus* species The effects of the compounds were approximately equipotent modest in both the sensitive and resistant isolates. (data not shown).

Example 3

Antibacterial Effect of Dealkylated Phenothiazine or Thioxanthene Compounds on Clinical Isolates of Fungi The antibacterial effect of demethylated/dealkylated phenothiazine or thioxanthene compounds were studied by growth inhibition studies exposing cells to 0-32 µg/ml of drug. Each experiment was repeated in triplicate. MIC values represent the mean values of two separate triplicate experiments.

4 clinical isolates of *Candida* species (including 3 fluconazole resistant isolates) were subcultured for 24 h on Sabouraud glucose agar before susceptibility testing. Broth microdilution tests were performed according to NCCLS document M27-A (Ref: National Commitee for Clinical Laboratory Standards. (1997). *Reference Method for Broth Dilution Antifungal Susceptibility Testing of Yeasts: Approved Standard M27-A*. NCCLS, Wayne, Pa.). Microtitre plates were read spectrophotometrically at 530 nm, after mixing the wells by pipetting to resuspend yeast sediments. In this experiment, the MIC was defined as the lowest drug dilution resulting in 90% growth inhibition. Results are shown in Table 3 below.

TABLE 3

Antimicrobial effect dealkylated phenothiazine or thioxanthene compounds on multiresistant resistant and susceptible clinical isolates of *Candida* species.

| Structure | $R_2$ | n | $X_2$ | Hetero-cycle | MIC μ/ml Mean (range) |
|---|---|---|---|---|---|
| (thioxanthene structure with Cl, =CH-CH₂-CH₂-piperidine, NH) | Cl | 2 | H | piperidine | 1.0 (0.25-2.0) |
| (thioxanthene structure with Cl, =CH-CH₂-CH₂-piperidine, N-CH₂CH₂OH) | Cl | 2 | CH₂CH₂OH | piperidine | 1.5 (0.125-2.0) |

* Each group consists of 8 Multiresistant isolates, including fluconazole resistance, and 8 susceptible clinical isolates of *Candida* species.

The results show that the compounds tested exhibit strong antifungal activity against the clinical isolates of *Candida* species including all of the multi resistant isolates. The effects of the compounds were approximately equipotent modest in both the sensitive and resistant isolates. (data not shown)

Example 4a

Synergistic Effects of Dealkylated Phenothiazine or Thioxanthene Compounds

Materials and Methods:

The effect of the compounds was tested according to the methods described in WO2005/105145. In brief, cell growth was tested using the MIC susceptibility tests by use of the microdilution broth method in accordance to the NCCLS Guidelines (NCCLS Guidelines, Methods for Dilution Antimicrobial Susceptibility Tests for Bacteria That Grow Aerobically; Approved Standard, Sixth Edition, Volume 23; Number 2).

FIC:

The Fractional Inhibitory Concentration (FIC) index were calculated for each compound as described in WO2005/105145. Synergy was defined for Fractional Inhibitory Concentration (FIC) indices less than 0.5

Bacterial Isolates:

*Enterococcus faecalis*: 8 multidrug resistant in vivo-selected clinical isolates. Resistant to ampicillin, ciprofloxacin, gentamicin, and decreased or fully resistance to vancomycin. Expressing change in the cell wall precursor target as a major resistance mechanism (VanA gene expression).

*Staphylococcus aureus*: 8 (MRSA) in vivo-selected clinical isolates. Resistant to methicillin and beta-lactam antibiotics. Susceptible to teicoplanin chloramphenicol, fosfomycin, netilmicin and vancomycin.

*E. coli*: 8 in vivo-selected multidrug resistant clinical isolates of *E. coli*. Resistant to tetracycline, beta-lactams, fluoroquinolones, chloramphenicol and aminoglycoside Table 4a shows the synergistic effect of the tested compound 1, 2, 3 and 4 in combination with ciprofloxacin, gentamycin, tetracycline, and dicloxacillin, respectively, tested on resistant bacterial isolates. Synergy was defined for Fractional Inhibitory Concentration (FIC) indices less than 0.5 (*mean values).

| Strain (No) | Resistance | Antibiotic | Comp. 1 | Comp. 2 | Comp. 3 | Comp. 4 |
|---|---|---|---|---|---|---|
| *E. coli* (8) | MDR | Ciprofloxacin | 0.47 | 0.44 | 0.44 | 0.47 |
| | | Ampicillin | 0.47 | 0.47 | 0.44 | 0.44 |
| | | Gentamycin | 0.47 | 0.44 | 0.44 | 0.47 |
| | | Tetracycline | 0.47 | 0.47 | 0.44 | 0.44 |
| *S. aureus* (8) | MRSA | Dicloxacillin | 0.28 | 0.37 | 0.25 | 0.34 |
| *E. faecalis* (8) | MDR/VRE | Ciprofloxacin | 0.28 | 0.47 | 0.25 | 0.34 |
| | | Dicloxacillin | 0.28 | 0.47 | 0.25 | 0.34 |

*Compounds tested at concentrations corresponding ¼ of the MIC value.

The FIC indices for the compounds show that these compounds are synergistic in promoting the antibacterial effects of the anti-infective agents in the drug resistant cells. All of the FIC indices for the chemosensitising compounds assayed on drug-resistant cells were <0.5. Compound 3 was the most potent of all the tested chemosensitising compounds, followed by compound 1, compound 4 and compound 2. Thus the clinical use of the compounds in combination with an anti-infective agent would likely shift the MIC of this anti-infective agent for the DR cells to well-below the clinically achievable concentration, showing effective concentrations at concentrations down to 0.06 µg/ml. The anti DR effect was as expected most potent in resistant cells. However a remarkable antibiotic enhancing effect was shown also in the susceptible cells, strongly indicating that the anti DR effect of these chemosensitising compounds is not restricted to cells overexpressing efflux pumps or betalactamase and the anti DR mechanism is not restricted to these targets. FIC indices for antibiotic susceptible cells ranged from 0.47 to 1.0.

Example 4b

Synergistic Effects of Dealkylated Phenothiazine or Thioxanthene Compounds

The maximal obtained reversal of resistance and synergistic effect was tested as previously described.

Strains: Multiresistant clinical isolates of *S. aureus* and *S. epidermidis*, Ten strains in each group.

TABLE 4b

Maximal Reversal of resistance and synergistic effect of compounds 1-4. Median values, µg/ml.

| Antibiotic | MIC alone | MIC compound 2 0.98 ug/ml (Fold enhanced) | MIC plus compound 4 0.75 ug/ml (Fold enhanced) | MIC plus compound 1 0.60 ug/ml (Fold enhanced) | MIC plus compound 3 0.30 ug/ml (Fold enhanced) |
|---|---|---|---|---|---|
| Dicloxacillin & Methicillin | 64 | 4 (16) | 4 (16) | 4 (16) | 2 (32) |
| Benzylpenicillin | 64 | 8 (8) | 8 (8) | 8 (8) | 4 (16) |
| Ampicillin | 16 | 4 (4) | 4 (4) | 4 (4) | 2 (8) |
| Erythromycin | 16 | 4 (4) | 4 (4) | 4 (4) | 2 (8) |
| Tetracyclin | 16 | 8 (2) | 8 (2) | 4 (2) | 2 (4) |
| Gentamicin | 8 | 4 (2) | 4 (2) | 4 (2) | 2 (4) |
| Ciprofloxacin | 16 | 4 (4) | 4 (4) | 4 (4) | 1 (16) |

Maximal reversal of resistance means the concentration at which additional administration of compound does not lower the MIC any further. As seen, compound 3 is superior regarding the ability of reversal of resistance and synergistic effect in combination with common antimicrobials. At the lowest concentration, 0.30 µg/ml, compound 3 enhanced the antimicrobial activity of the combined antimicrobial to the highest degree, obtaining the highest fold of enhancement and lowest MIC values. Compounds 1, 2 and 4 all showed synergistic effect but to a lower degree, and at higher concentration (0.75 or 0.98 or 0.60 µg/ml). However, compound 4 was superior to compound 2 in that maximum reversal of resistance was reached at a lower concentration. All FIC values were below 0.5 in accordance with the synergistic effect obtained.

Example 4c

Synergistic Effects of Dealkylated Phenothiazine or Thioxanthene Compounds

Compound 3 is superior compared to transclopenthixol and N-dealkyl-transclopenthixol.

The maximal obtained reversal of resistance and synergistic effect was tested as previously described.

Strains: Multiresistant clinical isolates *E. coli*, Ten strains in each group.

TABLE 4c

Maximal Reversal of resistance and synergistic effect of Compounds 1-3. Median values, µg/ml.

| Antibiotic | MIC alone | MIC plus compound 2 2.0 ug/ml (Fold enhanced) | MIC plus compound 1 1.0 ug/ml (Fold enhanced) | MIC plus compound 3 0.6 ug/ml (Fold enhanced) |
|---|---|---|---|---|
| Ampicillin | 32 | 8 (4) | 4 (8) | 2 (16) |
| Piperacillin | 16 | 4 (4) | 4 (4) | 2 (8) |
| Tetracyclin | 16 | 4 (4) | 4 (4) | 2 (8) |
| Gentamicin | 8 | 4 (2) | 4 (2) | 2 (4) |
| Ciprofloxacin | 16 | 4 (4) | 4 (4) | 2 (8) |

As seen, compound 3 is superior regarding the ability of reversal of resistance and synergistic effect in combination with common antimicrobials. At the lowest concentration, 0.6 µg/ml, compound 3 enhanced the antimicrobial activity of the combined antimicrobial to the highest degree, obtaining the highest fold of enhancement and lowest MIC values. Compounds 1 and 2 both showed synergistic effect but to a lower degree, and at higher concentration used (2.0 or 1.0 µg/ml). All FIC values were below 0.5 in accordance with the synergistic effect obtained.

Example 5

Development of Insensitivity to the Chemosensitising Compounds

One potential limitation to the combination of an anti-infective agent with inhibitors of resistance mechanism(s) is the possibility of the microorganism developing mutations which render it insensitive to the inhibitor. Such a situation has been observed for e.g. bacteria, virus, fungi and yeast.

The effect of the inhibitors on the rate of emergence of in vitro-selected single-step ciprofloxacin resistance on the clinical isolate of *S. aureus* O11 was determined.

Spontaneous mutants were obtained 24 h after plating *S. aureus* cells on LB agar plates containing ciprofloxacin at a concentration of 1 µg/ml (two times the MIC) in the absence or presence of compound 3 (see Table 4) at 1 µg/ml. The frequency of mutant selection was determined to be $3 \times 10^{-8}$ by comparing the number of colonies that grew on plates containing the anti-infective agent with the number of colonies obtained upon plating appropriate dilutions in the absence of anti-infective agents.

The probably most important aspect, when assessing the use of the inhibitors in the clinic, is the effect of these inhibitors on the emergence of resistant mutants. Importantly, and as shown in Table 5, the tested inhibitor decreased the frequency of spontaneous emergence of ciprofloxacin resistance by 100-fold or more. This dramatic effect could not be attributed to a toxic effect of the inhibitor since the same concentration of inhibitor, which was at least 10-fold less than its MIC for *S. aureus*, affected neither the colony-forming ability nor the colony size of *S. aureus* cells plated in the absence of ciprofloxacin. In conclusion, the trans-clopenthixol inhibited the emergence of ciprofloxacin resistance in *S. aureus*.

TABLE 5

Frequency of emergence of in vitro-selected variants of *S. aureus* resistant to 1 μg of ciprofloxacin per ml (two times the MIC for the *S. aureus* strain) in either the absence or the presence of inhibitor.

| Inhibitor | Frequency of emergence of resistance |
|---|---|
| None | $3 \times 10^{-8}$ |
| Compound 3 (1 μg/ml) | $<1 \times 10^{-10}$ |

Example 6

Anti-Microbial Effect of Compound 3 in a Mouse Peritonitis Model

Mouse peritonitis/sepsis model.
Bacteria.

A clinical isolate of *Enterococcus faecalis* BG VSE-92 from human urine was used. This strain is a multiresistant isolate.
Animals.

Female NMRI mice (age, approximately 6 to 8 weeks; weight, 30±2 g) were used for the mouse pneumonia peritonitis model (as described below).

Bacterial suspensions were prepared from fresh overnight cultures (made from frozen stock cultures) on 5% blood agar plates as described above. The inoculum for the mouse peritonitis model was prepared immediately before use and was adjusted at 540 nm of giving a density of approximately 107 CFU/ml. The size of the inoculum was determined by viability counting on 5% blood agar.

The mice were injected intraperitoneally with 0.5 ml of the enterococcal suspension, resulting in bacteremia within 1 h of inoculation. Antibiotic therapy was initiated 1 h after inoculation. N-dealkyl-Trans-clopenthixol was administered subcutaneously in the neck region in a volume of 0.7 ml per dose. Five mice were in each treatment group. Inoculated untreated control mice were included in all trials. (Method reference: Erlandsdottir et al; Antimicrob Agents Chemother. 2001 April; 45(4):1078-85)

TABLE 6

Treatment regimes of infected mice.

| Groups | Treatment |
|---|---|
| Controls | None or vehicle (0.9% NaCl) |
| Compound 3 | 3.1 mg /kg s.c. |

The effects of the various treatment regimens were determined during 5 h of treatment by evaluation of bacterial counts in the peritoneal fluid. The bactericidal efficacies of the treatment regimens in the mouse models were calculated by subtracting the results for each treated mouse from the mean results for control mice at the end of therapy (5 h). A decrease of one thousand times (3 log 10 steps) represents maximum effect in this model and sustains strong bacterial killing effect of the compound tested.
Results:

Strong anti-microbial activity of compound 3 in infected mouse.

The bactericidal activity of compound 3 in mouse peritoneal fluid is shown in Table 7. As seen, when the mice were treated with the compound, the number of bacteria per ml of peritoneal fluid decreased 3 log 10 steps, and only 0.001% of the bacteria survived after 5 hours. ($p<0.05$).

TABLE 7

Bacteria/ml of peritoneal fluid in treated and non-treated infected mice, 5 hours after inoculation.

| mouse no. | dose | Time of treatment | Time of sampling | CFU/ml - peritoneum |
|---|---|---|---|---|
| 1 | None | None | 1 hour after inoculation | 1.13E+08 |
| 2 | | | | 1.30E+08 |
| 3 | | | | 1.10E+08 |
| 4 | Vehicle | 0 and 1 hour | 5 hours | 3.85E+09 |
| 5 | 0.9% NaCl | | | 3.75E+09 |
| 6 | | | | 1.30E+09 |
| 7 | compound 3; | 0 and 1 hour | 5 hours | 2.05E+06 |
| 8 | 3.1 mg/kg | | | 2.90E+06 |
| 9 | s.c | | | 4.25E+06 |

Inoculum used: $1.28 \times 10^8$ CFU/ml

Example 7

Enhancing Effect of Compound 3 in a Mouse Peritonitis Model

Bacteria

A multiresistant clinical isolate of *Enterococcus faecalis* ENT 28 (VRE) from human urine was used.
Animals.

Female NMRI mice (age, approximately 6 to 8 weeks; weight, 30±2 g) were used for the mouse pneumonia peritonitis model (as described below).
Antibiotics.

Linezolid was obtained from Sigma, Denmark, as a dry powder.
Mouse Peritonitis Model.

In order to detect any synergistic effect, infected mice were treated with sub-therapeutic doses of each test compound alone or a mixture of the two compounds.

Bacterial suspensions were prepared from fresh overnight cultures (made from frozen stock cultures) on 5% blood agar plates as described above. The inoculum for the mouse peritonitis model was prepared immediately before use and was adjusted at 540 nm of giving a density of approximately 107 CFU/ml. The size of the inoculum was determined by viability counting on 5% blood agar.

Neutropenia was introduced by pretreating the mice with cyclophosphamide (6 mg daily for three days). The mice were injected intraperitoneally with 0.5 ml of the enterococcal suspension, resulting in bacteremia within 1 h of inoculation. Antibiotic therapy was initiated just after inoculation. Linezolid and compound 3 was administered subcutaneously in the neck region in a volume of 0.5 ml per dose. 3 mice were in each treatment group. Inoculated untreated control mice were included in all trials. (Method reference: Erlandsdottir et al; Antimicrob Agents Chemother. 2001 April; 45(4):1078-85)

TABLE 8

Treatment regimes of infected mice.

| Group | Treatment |
|---|---|
| 1. Control | None |
| 2. Linezolid alone | 15 mg/kg per mouse |
| 3. compound 3 alone | 1.5 mg/kg per mouse |

TABLE 8-continued

Treatment regimes of infected mice.

| Group | Treatment |
|---|---|
| 4. Linezolid and compound 3 | 1.5 mg per kg mouse of compound 3 immediately followed by 15 mg per kg of Linezolid per mouse |

The effects of the various treatment regimens were determined during 5 h of treatment by evaluation of bacterial counts in the peritoneal fluid. After the mice were killed, peritoneal washes were performed by injecting 2 ml of sterile saline intraperitoneally, followed by massage of the abdomen and then opening of the peritoneum to collect the fluid. Peritoneal fluids were immediately diluted 10-fold in saline, from which 20 µl was plated onto 5% blood agar plates in spots, with subsequent counting of colonies after incubation overnight at 35° C. The lowest detection levels for bacterial counts in blood and peritoneal fluid were 50 and 250 CFU/ml, respectively. The bactericidal efficacies of the treatment regimens in the mouse models were calculated by subtracting the results for each treated mouse from the mean results for control mice at the end of therapy (5 h). A decrease of one thousand times (3 log 10 steps) represents maximum effect in this model and sustains strong bacterial killing effect of the compounds tested.

Results:

Strong Enhancing activity of compound 3 in mouse peritoneum.

The bactericidal activity of Linezolid and compound 3, alone or in combination, in mouse peritoneum is shown in Table 9. As seen, linezolid alone in sub-therapeutic dose had no effect on the infection and the resistant bacteria are not eradicated from the mouse peritoneum. But when the mice were treated with linezolid and compound 3 in combination the bacteria was eradicated and less than 0.001% was left alive (p<0.05). Compound 3 alone did not affect the bacteria in accordance with the sub-therapeutic dose given.

Example 8

Synergistic Effects of Dealkylated Phenothiazine or Thioxanthene Compounds on Fungals Antifungal Agent: Fluconazole (Pfizer, Ballerup, Denmark)

The isolates were subcultured for 24 h on Sabouraud glucose agar before susceptibility testing.

Broth microdilution tests were performed according to NCCLS document M27-A (Ref: National Commitee for Clinical Laboratory Standards. (1997). Reference Method for Broth Dilution Antifungal Susceptibility Testing of Yeasts: Approved Standard M27-A. NCCLS, Wayne, Pa.)

Microtitre plates were read spectrophotometrically at 530 nm, after mixing the wells by pipetting to resuspend yeast sediments. The MIC was defined as the lowest drug dilution resulting in 80% growth inhibition for fluconazole. The following tentative break-points were applied: fluconazole susceptible (S), MIC≤8 mg/L; susceptible dose-dependent (SDD), MIC>8-<64 mg/L; and resistant (R), MIC≥164 mg/L The Fractional Inhibitory Concentration (FIC) was calculated for the anti-infective agent alone and in combination with compound 3 and 4 (see table 4) as described above. Synergy was defined as a FIC index of <0.5. The calculated FIC index are shown in Table 10 below

TABLE 10A

Synergistic effects of compound 3 on Candida albicans

| Fungal Strain | MIC µg/ml Fluconazole (FL) | MIC µg/ml Compound 3 | MIC µg/ml FL + comp 3 (0.25 µg/m1) | FIC index |
|---|---|---|---|---|
| Candida albicans | 128 | 1 | 4 | 0.28 |

TABLE 10B

Synergistic effects of compound 4 on Candida albicans

| Fungal Strain | MIC µg/ml Fluconazole (FL) | MIC µg/ml Compound 4 | MIC µg/ml FL + comp 3 (0.50 µg/ml) | FIC index |
|---|---|---|---|---|
| Candida albicans | 128 | 1.5 | 8 | 0.39 |

TABLE 9

Enhancing effect of compound 3 in a mouse peritonitis model

| mouse no. | dose | Time of treatment | Time of sampling | score at sampling | Cfu/ml peritoneum | log (cfu/ml) peritoneum |
|---|---|---|---|---|---|---|
| 1 | None | None | 1 hour after inoculation | 1 | 6.75E+07 | 7.83 |
| 2 | | | | 1 | 7.50E+07 | 7.88 |
| 3 | | | | 2 | 8.75E+07 | 7.94 |
| 19 | | | | 2 | 7.50E+07 | 7.88 |
| 20 | | | | 2 | 4.50E+07 | 7.65 |
| 4 | Vehicle | 0 and 2 hours | 5 hours | 1 | 3.53E+09 | 9.55 |
| 5 | | | | 1 | 2.95E+09 | 9.47 |
| 6 | | | | 2 | 3.48E+09 | 9.54 |
| 7 | Linezolid | 0, and 2 hours | 5 hours | 2 | 2.08E+09 | 9.32 |
| 8 | 1 mg/ml, | | | 3 | 2.20E+09 | 9.34 |
| 9 | 0.5 ml | | | 3 | 2.40E+09 | 9.38 |
| 10 | Compound 3 | 0 and 2 hours | 5 hours | 1 | 2.35E+09 | 9.37 |
| 11 | 0.1 mg/ml | | | 2 | 2.63E+09 | 9.42 |
| 12 | 0.5 | | | 2 | 3.15E+09 | 9.50 |
| 16 | Linezolid | 0 and 2 hours | 5 hours | 0 | 1.90E+03 | 3.28 |
| 17 | 2 mg/ml, (0.25 ml) and compound 3 | | | 0 | 5.00E+01 | 1.70 |
| 18 | 0.2 mg/ml, (0.25 ml) | | | 0 | 1.18E+03 | 3.07 |

The FIC index for compound 3 and 4 shows that these compounds are synergistic in promoting the antifungal effect of the anti-fungal agents in the drug resistant cells. As seen the FIC index for the chemosensitising compounds assayed on drug-resistant cells were <0.5. Thus the clinical use of e.g. compound 3 or 4 in combination with an anti-fungal agent would likely shift the MIC of this anti-fungal agent for the DR cells to well-below the clinically achievable concentration, showing effective concentrations at <0.5 μg/ml.

Example 9

Enhancing Effects of Compound 3 on Anti-Viral Compounds

The enhancing effect of compound 3 on anti-viral agents was studied by checkerboard combination studies exposing HIV infected cells to 0-3 μM anti-viral agent in the absence or presence of compound 3 in concentrations from 0 to 6 μM. Each experiment was repeated in tripleduplicate. MIC values represent the mean values of two separate experiments.
Methods:
Viruses and Cells.

The HIV-1 strain HTLV-IIIB were propagated in H9 cells at 37° C., 5% CO2 using RPMI 1640 with 10% heat-inactivated foetal calf serum (FCS) and antibiotics (growth medium). Culture supernatant was filtered (0.45 nm), aliquotted, and stored at −80° C. until use. The HIV-1 strain was obtained from NIH AIDS Research and Reference Program.
Compounds.

Antiviral drug: AZT, (3'-Azido-3'-deoxythymidine), Glaxo Wellcome.

Enhancing compound: Trans-clopenthixol was obtained as a powder reference substance from British Pharmacopoeia Commission Laboratory, Middlesex, United Kingdom.
Inhibition of HIV-1 Replication.

Compounds were examined for possible antiviral activity against strain IIIB of HIV-1 using MT4 cells as target cells. MT4 cells were incubated with virus (0.005 MOI) and growth medium containing the test dilutions of compound(s) for six days in parallel with virus-infected and uninfected control cultures without compound added. Expression of HIV in the cultures was indirectly quantified using the MTT assay as previously described. Compounds mediating less than 30% reduction of HIV expression were considered without biological activity. Compounds were tested in parallel for cytotoxic effect in uninfected MT4 cultures containing the test dilutions of compound as described above. Cultures for test of both antiviral activity and cytotoxic effect were set up in tripleduplicates, 200 ml per culture in micro titre plates. A 30% inhibition of cell growth relative to control cultures was considered significant. The 50% inhibitory concentration was determined by interpolation from the plots of percent inhibition versus concentration of compound.

EC50 is defined as the effective concentration that inhibits 50% of viral production, 50% of viral infectivity, or 50% of the virus-induced cytopathic effect.

CC50 is defined as the inhibitory concentration that reduces cellular growth or viability of uninfected cells by 50%.
Results As seen in Table 11, the combination of compound 3 (see table 4) and AZT resulted in a 5 time enhancement of the antiviral effect of AZT and thus may be sufficient to inhibit resistant viral strains. Compound 3 alone had no antiviral or cytotoxic effect at the concentrations used.

TABLE 11

Enhancing effect of compound 3 (C3) on an antiviral compound AZT (A). Concentrations in μM.

| EC50 A | CC50 A | EC50 C3 | CC50 C3 | EC50 A + C3 (1 μM) | CC50 A + C3 (1 μM) |
|---|---|---|---|---|---|
| 0.05 | >3 | >4 | >4 | 0.01 | >3 |

EC50 is defined as the effective concentration that inhibits 50% of viral production, 50% of viral infectivity, or 50% of the virus-induced cytopathic effect
CC50 is defined as the inhibitory concentration that reduces cellular growth or viability of uninfected cells by 50%.

Viral test Method Reference: Petersen L, Jørgensen P T, Nielsen C, Hansen T H, Nielsen J, Pedersen E B. Synthesis and Evaluation of Double-Prodrugs against HIV. Conjugation of D4T with 6-Benzyl-1-(ethoxymethyl)-5-isopropyluracil (MKC-442, Emivirine) Type Reverse Transcriptase Inhibitors via the SATE Prodrug Approach. J. Med. Chem. 2005, 48, 1211-1220.

The invention claimed is:

1. A compound of formula (I)

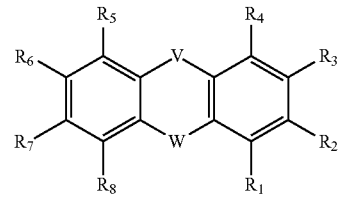

wherein

V is selected from the group consisting of S and NH;

W is C=CH—(CHX)$_n$—CX(R$_9$)(R$_{10}$), or W is C=CH—(CHX)$_{n-1}$—CH=C(R$_9$)(R$_{10}$);

n is an integer in the range of from 1 to 5;

each X is hydrogen;

R$_1$, R$_3$, R$_4$, R$_5$, R$_6$, R$_7$ and R$_8$ are hydrogen;

R$_2$ is selected from the group consisting of F, Cl, Br, I, CH$_2$Y, CHY$_2$, and CY$_3$, wherein Y is a halogen atom; and R$_9$ and R$_{10}$ together with the carbon atom to which they are attached form an optionally substituted C$_{3-6}$-cycloalkyl or C$_{3-6}$-heterocyclyl; or a salt thereof.

2. The compound according to claim 1, wherein n is 2, 3, or 4.

3. The compound according to claim 1, wherein R$_9$ and R$_{10}$ together with the carbon atom to which they are attached form an optionally substituted piperazinyl or piperidinyl.

4. The compound according to claim 3, wherein R$_9$ and R$_{10}$ together with the carbon atom to which they are attached form an optionally substituted piperidinyl.

5. The compound according to claim 1, wherein R$_9$ and R$_{10}$ together with the carbon atom to which they are attached form an optionally substituted nitrogen-containing heteroaryl or optionally substituted heterocyclyl wherein the nitrogen atom is separated by two carbon atoms from the carbon atom to which R$_9$ and R$_{10}$ are attached.

6. The compound according to claim 1, of formula (II)

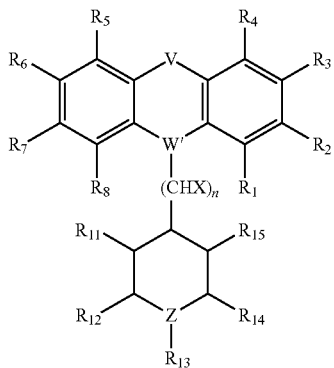

wherein;
V is selected from the group consisting of S and NH;
W' is C═CH;
n is an integer in the range of from 1 to 5;
each X is hydrogen;
Z is C, N, S, or O;

$R_1$, $R_3$, $R_4$, $R_5$, $R_6$, $R_7$, $R_8$, $R_{11}$, $R_{12}$, $R_{14}$ and $R_{15}$ are each hydrogen; and $R_{13}$ is hydrogen, halogen, hydroxy, amino, nitro, optionally substituted $C_{1-6}$-alkyl, or optionally substituted $C_{1-6}$-alkoxy; or
a salt thereof.

7. A pharmaceutical composition for the treatment of a bacterial infection, comprising the compound of claim 1 and an additional anti-infective agent.

8. A method for treating a bacterial infection in a subject, comprising:
administering to the subject a therapeutically effective amount of the compound of claim 1.

9. A pharmaceutical composition comprising the compound of claim 1, and at least one pharmaceutically acceptable carrier or excipient.

10. The pharmaceutical composition of claim 9, further comprising at least one additional anti-infective agent.

11. A method for treating a bacterial infection in a subject, comprising:
administering to the subject a therapeutically effective amount of the compound of claim 9.

* * * * *